United States Patent
Kobashi et al.

(10) Patent No.: US 8,232,527 B2
(45) Date of Patent: Jul. 31, 2012

(54) IMAGE GENERATION METHOD AND DEVICE FOR EMISSION COMPUTED TOMOGRAPHY

(75) Inventors: Keiji Kobashi, Mito (JP); Wataru Takeuchi, Hitachi (JP)

(73) Assignee: Hitachi, Ltd., Tokyo (JP)

( * ) Notice: Subject to any disclaimer, the term of this patent is extended or adjusted under 35 U.S.C. 154(b) by 519 days.

(21) Appl. No.: 12/388,943

(22) Filed: Feb. 19, 2009

(65) Prior Publication Data

US 2009/0242776 A1 Oct. 1, 2009

(30) Foreign Application Priority Data

Mar. 26, 2008 (JP) .................. 2008-081500

(51) Int. Cl.
*G01T 1/161* (2006.01)
*G01T 1/166* (2006.01)
*G01N 23/00* (2006.01)

(52) U.S. Cl. ......... 250/363.02; 250/363.07; 250/363.04; 378/4; 378/21

(58) Field of Classification Search ............. 250/363.02, 250/363.04, 363.07; 378/4, 21
See application file for complete search history.

(56) References Cited

U.S. PATENT DOCUMENTS

| | | | |
|---|---|---|---|
| 7,053,376 B2 | 5/2006 | Amemiya et al. | |
| 7,117,026 B2 | 10/2006 | Shao et al. | |
| 7,251,523 B2 | 7/2007 | Kojima et al. | |
| 7,292,673 B2 * | 11/2007 | Kroner et al. | 378/20 |
| 7,397,934 B2 | 7/2008 | Bloch et al. | |
| 7,593,558 B2 | 9/2009 | Boese et al. | |
| 2003/0012331 A1 | 1/2003 | Kojima et al. | |
| 2007/0230761 A1 * | 10/2007 | Gundel et al. | 382/131 |
| 2008/0031405 A1 * | 2/2008 | Matsumoto | 378/8 |
| 2008/0234575 A1 * | 9/2008 | Klingenbeck-Regn et al. | 600/431 |
| 2009/0182224 A1 * | 7/2009 | Shmarak et al. | 600/424 |

FOREIGN PATENT DOCUMENTS

| | | |
|---|---|---|
| JP | 52-155889 A | 12/1977 |
| JP | 2003-90882 | 3/2003 |
| JP | 2003-232855 | 8/2003 |
| JP | 2005-106507 | 4/2005 |
| JP | 2005-291814 | 10/2005 |
| JP | 2006-231083 | 9/2006 |

(Continued)

OTHER PUBLICATIONS

Eur. J Nucl. Med. Mol. Imaging (2007) 34:1447-1454.

(Continued)

*Primary Examiner* — David Porta
*Assistant Examiner* — Mindy Vu
(74) *Attorney, Agent, or Firm* — Mattingly & Malur, PC

(57) ABSTRACT

A first γ-ray generating in a body, caused by a PET pharmaceutical, and a second γ-ray emitted from a γ-ray source and transmitting through the body are detected with a radiation detector. The emission image information (E image information), $E_0$, $E_1$ and $E_2$, at each of patient motion phases, 0, 1 and 2, which divided a respiration period, are prepared by using information obtained from the detected first γ-ray. The transmission image information (T image information), $T_0$, $T_1$ and $T_2$, at each of patient motion phases, 0, 1 and 2, respectively, are prepared, by using information obtained from the detected second γ-ray. Relative displacements, ($[F_{10}]$, $[F_{20}]$), are determined by superimposing, on T image information $T_0$, other T image information, $T_1$ and $T_2$. The E image information, $E_1$, $E_2$, are superimposed on the E image information $E_0$, by using this relative displacement.

20 Claims, 7 Drawing Sheets

FOREIGN PATENT DOCUMENTS

JP  2006-300938 A  11/2006
JP  2007-181729 A  7/2007

OTHER PUBLICATIONS

IEEE Transactions on Medical Imaging, vol. 18, No. 8, Aug. 1999.
The Journal of Nuclear Medicine vol. 43, No. 7, Jul. 2002, pp. 876-881.
The Journal of Nuclear Medicine vol. 45, No. 2, Feb. 2004, pp. 214-219.
The Journal of Nuclear Medicine vol. 45, No. 1 (Suppl) Jan. 2004, pp. 4S-14S.
"Reconstructing Interior Head Tissue From X-Ray Transmissions" by L. A. Shepp, et al., Feb. 1974, pp. 228-229.
"The CT Motion Quantitation of Lung Lesions and its Impact on PET-Measured SUVs" by Y. Erdi, et al, Feb. 5, 2004, pp. 1287-1292.

* cited by examiner

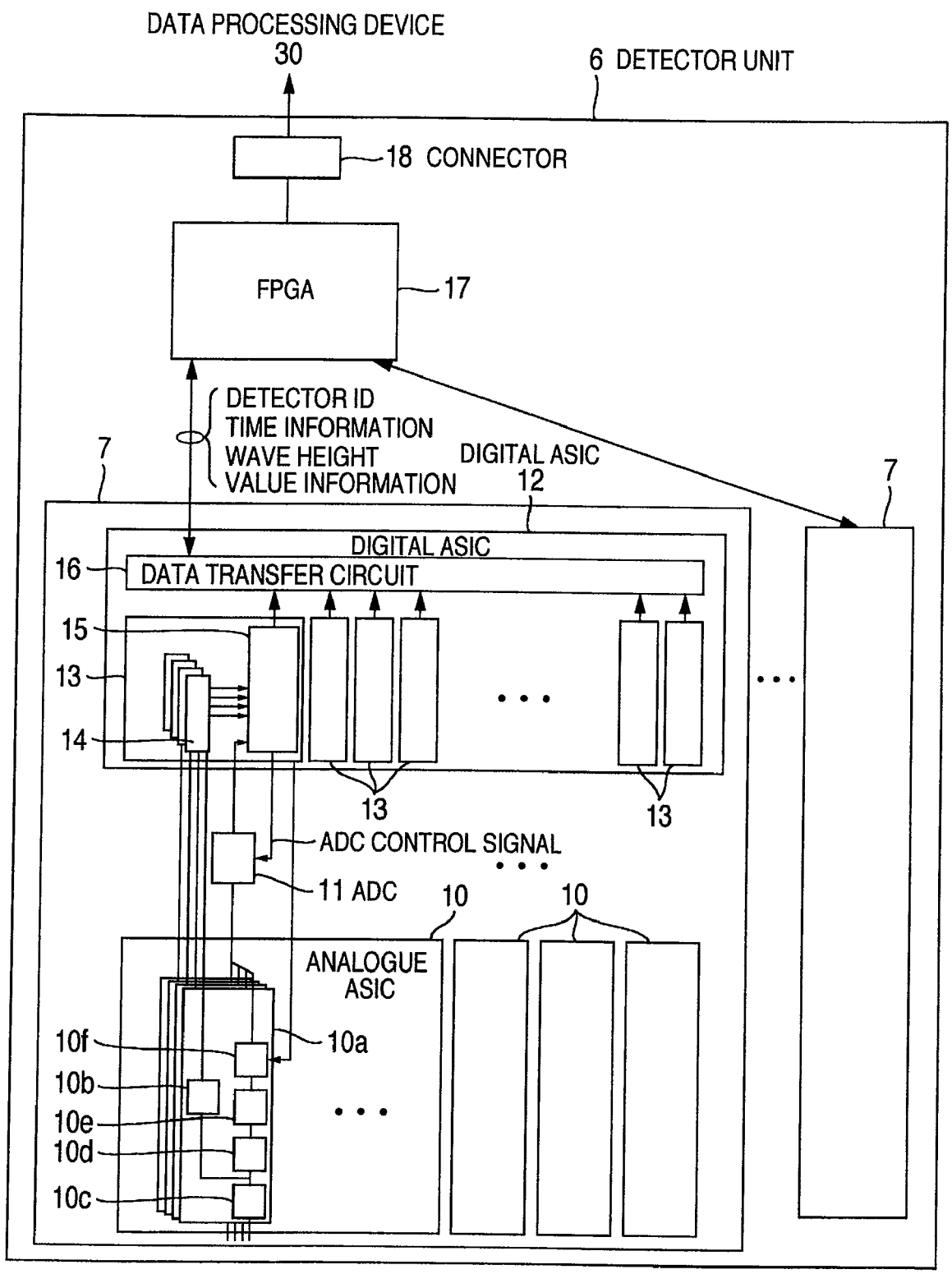

IMAGE GENERATION METHOD AND DEVICE FOR EMISSION COMPUTED TOMOGRAPHY

BACKGROUND OF THE INVENTION

The present invention relates to a preparation method for image information by an image processing device.

A PET device has been used, as an important tool, mainly for the object of diagnosis of malignant tumors in the medical field, in recent years. The PET device measures radiation (γ-ray) emitted from the inside of a patient body, derived from a radiopharmaceutical injected into a patient as a subject body, and images distribution of the radiopharmaceutical in the patient body from measurement data thereof. Such a PET device is used in diagnosis of metabolic function and physiologic function. As a typical radiation image diagnosis device, which applies radiation measurement technology, for noninvasively obtaining an image of the inside of the patient, there is an X-ray CT device.

The PET device is equipped with many radiation detectors, and is required to process a huge amount of radiation detection signals (γ-ray detection signals), which are output from these radiation detectors. The quality of obtained image information has been limited from restriction of data processing, because image information (PET image information) is reconstructed by processing of the huge amount of data obtained by these radiation detection signals. However, with the rapid progress of signal processing circuit and computer technology, in recent years, image information with high quality has been enabled to be provided.

Diagnosis of a malignant tumor using the PET device is executed as follows. Firstly, the radiopharmaceutical, labeled with a positron emission nuclei species ($^{15}$O, $^{13}$N, $^{11}$C, $^{18}$F and the like), which specifically accumulates at a specific moiety in a body (hereafter called a PET pharmaceutical), is administered to the patient. A positron, which is emitted from the PET pharmaceutical in the patient body, experiences positron annihilation by binding with an electron inside of a nearby cell. In this annihilation, a pair of γ-rays (hereafter called pair γ-rays) having an energy of 511 keV are emitted. Because each of the pair of γ-rays is emitted in a nearly opposite direction to each other, it can be specified by coincidence counting of both γ-rays, at what position inside the body the positron annihilation event occurred. These γ-rays are detected with the radiation detectors. After the detection of a statistically sufficient number of the pair γ-rays, occurrence frequency distribution of the pair γ-rays, that is distribution of the PET pharmaceutical inside the patient body, can be imaged, by using an image information reconstruction algorithm, such as a filtered-back-projection method (refer to IEEE Transactions on Nuclear Science, Vol. NS-21, pages 228 to 229). Measurement of the γ-rays to be generated, caused by the PET pharmaceutical inside the body, is called emission measurement (hereafter called E measurement), and image information reconstructed, based on γ-ray detection signals obtained by the emission measurement, is called emission image information (hereafter called E image information). The E image information is generally called simply PET image, however, in the present description, to differentiate from transmission image information (hereafter called T image information) to be described later, it is called E image information. In addition, a series of processes from E measurement to reconstruction is called emission imaging collectively.

In an inspection using such a PET device, for example, in the case where the patient is administered with a PET pharmaceutical called FDG (Fluoro-2-deoxyglucose), which is an analog of a saccharide (glucose), the PET pharmaceutical is accumulated at a malignant tumor having a larger saccharide metabolism as compared with a normal moiety. Therefore, diagnosis of position and shape of malignant tumor becomes possible.

Incidentally, in an inspection using the PET device (PET inspection), which requires quantitativeness, in addition to E measurement, there is also executed a measurement called transmission (the transmission measurement, hereafter called T measurement), by using a γ-ray source, which is a transmission radiation source installed at the PET device. Attenuation of a γ-ray in the PET measurement indicates a phenomenon where a γ-ray derived from the radiopharmaceutical is not detected as coincidence count data effective in imaging, as a result of impact of interaction thereof with substances inside a body, before emission outside a patient body. A process to compensate this attenuated amount of this γ-ray is called attenuation compensation, and at present, it is executed in most of the PET inspections.

The attenuation compensation usually uses data obtained by T measurement. That is, by rotating a γ-ray source around the patient lying on a bed, γ-ray radiation emitted from the γ-ray source is irradiated onto the patient. Each of radiation transmittances in various directions, which this γ-ray radiation transmits through the patient, is determined. Data obtained by E measurement is compensated by using data of these radiation transmittances. As the γ-ray source, a radioisotope (hereafter called "RI") such as $^{68}$Ge-$^{68}$Ga and $^{137}$Cs is usually used. Instead of the γ-ray source, an X-ray source, described in JP-A-2006-231083, may also be used. It should be noted that, if necessary, tomographic image information of the patient is reconstructed, based on data obtained by T measurement. This tomographic image information is a morphological image, and is called hereafter T image information. The T image information is one representing distribution of radiation attenuation inside a patient body. If necessary, attenuation rates by each projection direction may be determined again based on the image information, and be used for attenuation compensation of these attenuation rates.

In recent years, a combined PET/CT device has been proposed, where an X-ray CT device is arranged in parallel to and combined with a PET device. This combined PET/CT device executes attenuation compensation by utilization of tomographic image information obtained by the X-ray CT device. JP-A-2006-231083 has proposed a PET device with a structure rotating an X-ray source inside a plurality of radiation detectors arranged circularly. This PET device also executes attenuation compensation by utilization of tomographic image information reconstructed by using detection signals of X-rays emitted from the X-ray source and transmitted through the patient.

As a large factor decreasing quality of E image information, impact of movement of a patient (hereafter called patient motion) is included. In the patient motion, there is periodic movement accompanied with involuntary respiration and heart beat, and a voluntary posture change. Because the PET inspection requires a long measurement time, usually from several minutes to several tens of minutes, it is difficult to suppress patient motion, without giving stress to the patient. In particular, because motion by respiration (hereafter called respiration motion) reaches as large as 2 to 3 cm, even in resting respiration, impact of patient motion on E image information is large in the PET inspection of a moiety near a lung field.

As a method for compensating blurring of image information accompanied with periodical patient motion such as respiration, a method called gated-acquisition has been known. The gated-acquisition is a method for dividing data of E measurement measured over a plurality of patient motion period amounts for each data of patient motion phases, and reconstructing E image information by each patient motion phase, respectively, by using these divided data. For example, in gated-acquisition for respiratory motion, as described in The Journal of Nuclear Medicine, Vol. 45, No. 2, pages 214 to 219, minute change of breath temperature is captured, and as described in The Journal of Nuclear Medicine, Vol. 43, No. 7, pages 876 to 881, movement of the body surface of a chest part is traced with an infrared stereo camera, or the like, and thus respiration phase information is obtained, and data obtained by E measurement, based on this phase information, is divided by each of the patient motion phases.

As another method for compensation of respiratory motion, there is a method for using the combined PET/CT device (refer to The Journal of Nuclear Medicine, Vol. 45, No. 8, pages 1287 to 1292). In The Journal of Nuclear Medicine, Vol. 45, No. 8, pages 1287 to 1292, attenuation compensation is executed by X-ray CT imaging in a cinema-mode, in the complex PET/CT device to obtain E image information by each respiration phase, and by using an X-ray CT image at a corresponding respiration phase, in preparing phase image information of each E image information by the gated-acquisition. It should be noted that, in IEEE Transactions on Medical Imaging, Vol. 18, No. 8, pages 712 to 720, a non-linear superimposing technology for two image informations (Non-rigid image registration method) has been disclosed.

SUMMARY OF THE INVENTION

By execution of gated-acquisition, as described above, in E measurement, it is possible to compensate, in principle, the impact associated with periodic patient motion. However, in order to obtain data with sufficient statistical accuracy for each patient motion phase, a long measurement time is required. Because the PET inspection over a long time gives pain to the patient (in many cases, the patient with diseases), the PET inspection is completed usually in about 20 to 30 minutes. In this case, only measurement data for several minutes or shorter, at the most, can be obtained for each patient motion phase (refer to The Journal of Nuclear Medicine, Vol. 45, No. 2, pages 214 to 219). Accordingly, E image information obtained by reconstruction of each data contains statistical noises to a great extent. In the case where filtering is executed in an imaging process to suppress the statistical noises, blurring is generated in the image information. By decreasing the number of patient motion phases to be divided, statistical accuracy per unit patient motion phase can be enhanced. However, it increases patient motion within one patient motion phase time, and in the first place, it is difficult to obtain the compensation effect for the patient motion. That is, in a simple gated-acquisition, effective patient motion compensation cannot actually be executed in a short time, and problems of (1) blurring of E image information and (2) decrease in quantitativeness of E image information basically cannot be solved.

In The Journal of Nuclear Medicine, Vol. 45, No. 2, pages 214 to 219, it has been described that it is possible to enhance statistical accuracy, by superimposing E image information obtained by gated-acquisition on image information of a certain determined phase with non-linear deformation, and superimposing pixel values. However, in The Journal of Nuclear Medicine, Vol. 45, No. 2, pages 214 to 219, there is no recognition of the difficulty in deforming E image information and superimposing them on each other. Different from a morphological image of image information to be reconstructed by X-ray CT, and T image information, etc., E image information does not intend to draw a structure inside a body. Therefore, it is generally extremely difficult to deform E image information for each of the patient motion phases and superimpose them on each other.

It is an object of the present invention to provide an image information preparation method enabling to provide more vivid functional image information of a living body with a target of a moiety receiving impact of patient motion, in a short time.

A characteristic of the present invention to attain the above objects is an image information preparation method for preparation of superimposed first image information, by preparing first image information, in which a function of a living body is imaged at a plurality of phases obtained by dividing a certain period in terms of time; by preparing second image information, in which a structure of a living body is imaged at a plurality of phases; by determining relative displacement information among the second image information thereof by superimposing, on the second image information at a certain one of the phases among a plurality of phases, the second image information at the other phases; and by superimposing, superimposed first image information on the first image information at a certain one of the phases, the first image information at the other phases, by using the relative displacement information.

According to the present invention, more vivid functional image information of a living body can be obtained, in a short time, with a target of a moiety receiving impact of patient motion.

BRIEF DESCRIPTION OF THE DRAWINGS

FIG. 7 is a perspective view showing a detailed configuration of the module substrate shown in FIG. 3.

DETAILED DESCRIPTION OF THE INVENTION

Figure 1:
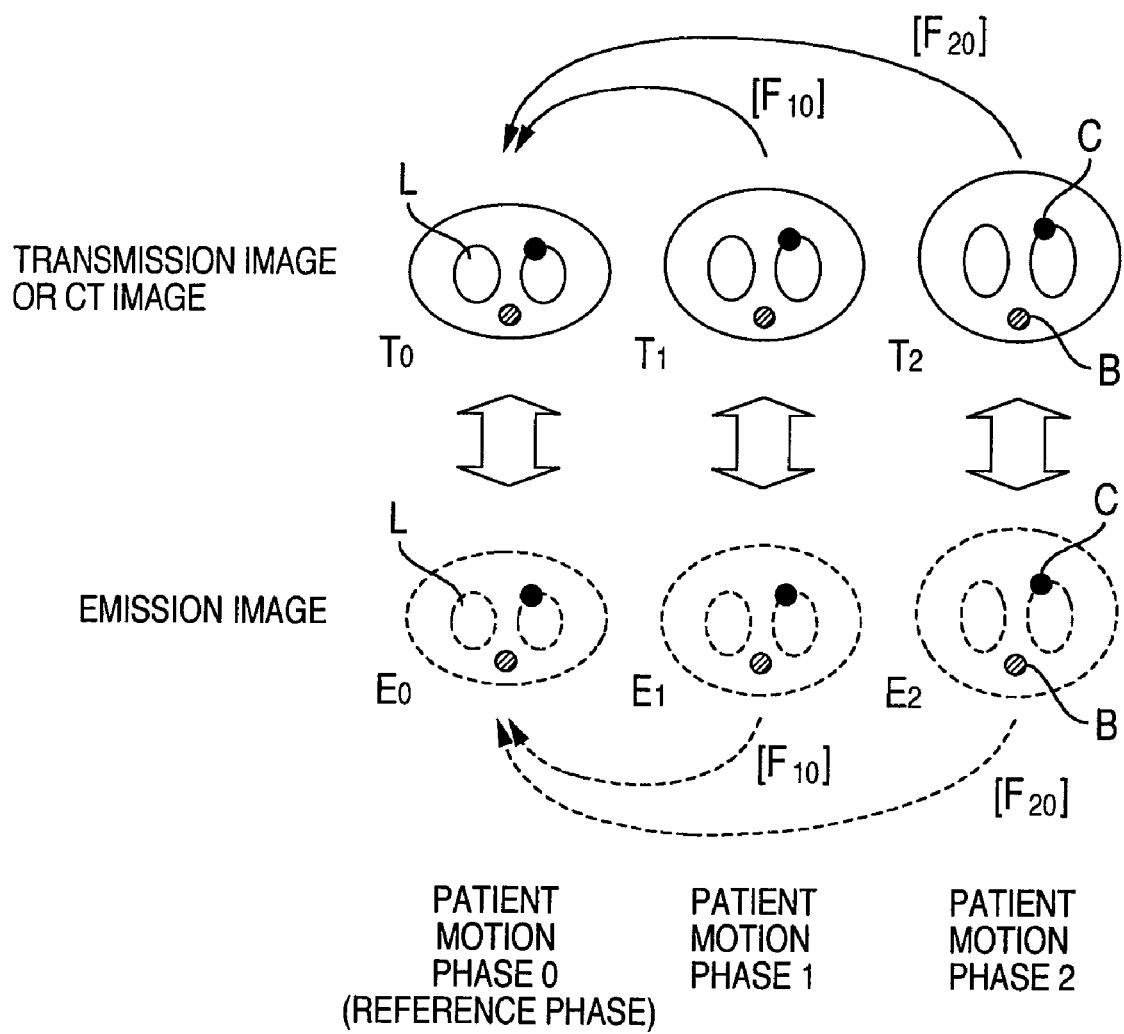
FIG. 1 is an explanation drawing of a respiratory motion compensation method according to the present invention.

Explanation will be given below on a positron emission-type computed tomography device, which is one embodiment of the present invention, with reference to the drawings, as appropriate.

Embodiment 1

As impacts given by respiratory motion on E image information, there are the following three:
(1) blurring of E image information
(2) decrease in quantitativeness of E image information
(3) position mismatch in superimposing an X-ray CT image taken under breath-holding and a PET image, at the periphery of a lung field.

The problems (1) and (2) among these have become main concerns as large factors impairing picture quality at present with the dramatic enhancement of the spatial resolution of the PET device. As for the problem (3), even at present with frequent experience of superimposing image information by the recently developed combined PET/CT device (refer to The Journal of Nuclear Medicine, Vol. 45, No. 1, pages 4S to 14S), solution thereof is still highly desired mainly in a field requiring specification of the position of a malignant tumor with good accuracy, such as in radiation therapy and biopsy.

The problem of (1) makes radiation therapy planning and evaluation of therapy effect difficult, due to blurring of the region of disease sites of internal organs and malignant tumors, or other disease moieties. In addition, even a small malignant tumor with relatively not high accumulation degree can be observed vividly within displayed E image information, in the case of no patient motion present. However, in the case of patient motion being present, such a malignant tumor is buried in statistical noises contained in the E image information, and makes it difficult to recognize even the presence thereof.

The problem of (2) underestimates the accumulation degree in general, for example, in a malignant tumor with large motion. In E image information, because the accumulation degree shown in a certain pixel at a position with large patient motion, becomes time-averaged-like accumulation degree of the peripheral moieties, it provides the accumulation degree different from practical value. Therefore, the accumulation degree becomes low as shown above.

The problem of (3) is a problem occurring in superimposing E image information obtained by imaging for several minutes under natural breathing, and an X-ray CT image taken in a short time under breath-holding. This superimposed image information is useful in diagnosis, however, at the periphery of a lung field; it is observed as an image with mismatch of up to about 1 cm at the maximum. This is because of the difference of the handling of respiration between the PET inspection and the usual X-ray CT inspection, and thus positional correspondence is not necessarily taken. This problem has been pointed out also in the PET/CT device, and a solution thereof has been desired.

By execution of gated-acquisition, as described above, in E measurement, it is possible to compensate for, in principle, impact associated with periodic patient motion. However, in order to obtain data with sufficient statistical accuracy for each patient motion phase, a long measurement time is required. Because the PET inspection over a long time gives pain to the patient (in many cases, the patient with diseases), the PET inspection is completed usually in about 20 to 30 minutes. In this case, only measurement data for several minutes or shorter, at the most, can be obtained for each patient motion phase (refer to The Journal of Nuclear Medicine, Vol. 45, No. 2, pages 214 to 219). Accordingly, E image information obtained by reconstruction of each data contains statistical noises to a great extent. In the case where filtering is executed in an imaging process to suppress the statistical noises, blurring is generated in image information. By decreasing the number of patient motion phases to be divided, statistical accuracy per unit patient motion phase can be enhanced. However, it increases patient motion within one patient motion phase time, and in the first place, it is difficult to obtain the compensation effect for patient motion. That is, in a simple gated-acquisition, effective patient motion compensation cannot actually be executed in a short time, and the problems of (1) and (2) basically cannot be solved.

In The Journal of Nuclear Medicine, Vol. 45, No. 2, pages 214 to 219, it has been described that it is possible to enhance statistical accuracy, by superimposing E image information obtained by gated-acquisition on image information of a certain determined phase with non-linear deformation, and superimposing pixel values. However, in The Journal of Nuclear Medicine, Vol. 45, No. 2, pages 214 to 219, there is no description of the specific method. Different from a morphological image of image information to be reconstructed by an X-ray CT, and T image information, etc., E image information does not intend to draw a structure inside a body. Therefore, it is generally extremely difficult to deform E image information for each of the patient motion phases and superimpose them on each other.

Still more, as pointed out by, for example, The Journal of Nuclear Medicine, Vol. 45, No. 2, pages 214 to 219, also in the case of executing gated-acquisition in E measurement, attenuation compensation is executed by using data of T measurement obtained by non-gated-acquisition in the PET device, and in the combined PET/CT device, it is executed by using an X-ray CT image taken in a state of breath-holding or natural breathing. Therefore a problem is generated that between data obtained by E measurement and data obtained by T measurement, an artifact is generated in attenuation compensation caused by the difference of a respiration state of a patient, or there is a deterioration of quantitativeness caused by the non-execution of correct compensation. In The Journal of Nuclear Medicine, Vol. 45, No. 2, pages 214 to 219, as for this problem, it has been suggested that T measurement using a γ-ray source, or gated-acquisition by X-ray CT becomes a solution. However, in The Journal of Nuclear Medicine, Vol. 45, No. 2, pages 214 to 219, there is not shown a specific method for the solution.

As a method for eliminating impact of respiratory motion in E measurement, it is known to image in a state where a patient holds his or her breathing for a predetermined time (breath-holding imaging). This is a method for reconstruction of an image by using data measured during a period when a patient holds his or her breathing. Because a period during which a patient can hold his or her breathing is about 30 seconds at the most, a patient is asked to hold his or her breathing several times, if necessary. According to this method, the above-described problems (1) to (3) can be solved. However, it forces breath-holding for a patient receiving the PET inspection, and gives tremendous pain to the patient.

Still more, to force breath-holding for a patient generates a problem in attenuation compensation. That is, because it is difficult to force breath-holding also in T measurement, E measurement is executed under breath-holding, and T measurement is executed under natural breathing. Based on this morphological difference, there are generated an artifact in attenuation compensation, and deteriorated quantitativeness caused by incorrect compensation.

A method for using the complex PET/CT device, described in The Journal of Nuclear Medicine, Vol. 45, No. 8, pages 1287 to 1292, generates a problem of increased exposure to radiation, because X-ray CT imaging, which requires irradiation of high dose amount originally, is executed for a relatively long time. This method also leaves a problem of insufficient statistical accuracy described in The Journal of Nuclear Medicine, Vol. 45, No. 2, pages 214 to 219, in E image information, and the problems of (1) and (2) basically cannot be solved. Still more, in the complex PET/CT device, there is time mismatching between E measurement by PET and measurement by X-ray CT. Therefore, the complex PET/CT device receives impact based on the time mismatching, such as posture change and variation of respiration of a patient in both measurements, and could generate positioning mismatch of attenuation compensation and image information.

In the PET inspection at the periphery of a lung field, it is indispensable to eliminate impact of patient motion, in particular, respiratory motion, to obtain E image information with good quality. Accordingly, various approaches described above may be considered, however, they have basically not reached any solution thereof.

It is an object of the present invention to provide a preparation method for tomographic image information of a positron emission computed tomography device, and a positron emission computed tomography device, which enables to provide more vivid emission image information in a short time, with a target of a moiety receiving impact of patient motion.

As described above, in the PET inspection at the periphery of a lung field, it is indispensable to eliminate impact of patient motion, in particular, respiratory motion, to obtain E image information with good quality. Accordingly, it is desirable to solve the following problems, in addition to the above problems (1) to (3):
(4) not to force unnatural breath-holding for the patient.
(5) not to generate an artifact derived from attenuation compensation, and deteriorated quantitativeness.
(6) to execute an inspection in a short time to a degree not to give pain to the patient.

Incidentally, as described in The Journal of Nuclear Medicine, Vol. 45, No. 2, pages 214 to 219, it has been suggested that by gated-acquisition of E image information, and by superimposing image information at each patient motion phase, on image information at a certain one of the patient motion phases, under deformation with non-linear strain, and adding pixel values of corresponding pixels, image information with high statistical accuracy and having respiratory motion compensated, may be obtained. If this is attained, problems (1) to (4) and (6) among the above problems can be solved. However, as described above, it is generally impossible to superimpose non-linear image information, with a clue of E image information having scarce morphological information. Accordingly, something should be worked out to solve this. In addition, it is preferable to solve also the problem of (5).

The present inventors have studied a method for enabling to execute non-linear superimposing of E image information. Explanation will be given below on the results of this study.

In order to obtain measurement data with high statistical accuracy, for each patient motion phase of periodic patient motion (respiratory motion or heart beat) in the patient, PET inspection over a long time is required. Therefore, it is difficult to obtain the measurement data, within a measurement period endurable by the general patient without generating pain. Accordingly the present inventors have noticed a fact that statistical accuracy can be enhanced by superimposing E image information for each patient motion phase obtained by gated-acquisition in emission measurement (hereafter called E gated-acquisition) in a shorter time, on image information of a certain one of the patient motion phases, and by superimposing each of pixel values. However, E image information originally has scarce morphological information, and E image information for each patient motion phase, which can be obtained, based on data obtained by gated-acquisition in a short time, has insufficient statistical accuracy. Therefore, it is difficult to execute non-linear superimposing of E image information directly among E image information for each of the patient motion phases.

The present inventors have noticed, after execution of various studies, that it is good to reconstruct T image information for each patient motion phase, by execution of gated-acquisition in transmission measurement (hereafter called T gated-acquisition), in parallel to E gated-acquisition. As a result, the present inventors have found a novel method for obtaining emission superimposed image information (hereafter called E superimposed image information), by utilization of transmission superimposed image information (hereafter called T superimposed image information) obtained by non-linear superimposing of T image information themselves for each of the patient motion phases, and by indirect and non-linear superimposing of a plurality of E image information themselves, for each of the patient motion phases thereof. It has been found that according to this novel method, non-linear superimposing of E patient motion can be executed.

Explanation will be given below in detail of the fundamental concept of the above novel method, which the present inventors have found, with reference to FIG. 1, which is an explanation drawing of a respiratory motion compensation method. In FIG. 1, for easy understanding, there is shown, as an example, the case of dividing a respiration period, which is a patient motion period, into three patient motion phases. In FIG. 1, B represents a backbone, C represents a malignant tumor, and L represents a lung.

$T_0$, $T_1$ and $T_2$ at the upper part of FIG. 1 represent T image information corresponding to patient motion phases 0, 1 and 2, respectively. This image information can be obtained by reconstruction of information obtained by gated-acquisition in transmission measurement. Here, information obtained by T gated-acquisition is the second detection information containing time information and radiation source position information, to be described later, and patient motion phase information provided with time information. $E_0$, $E_1$ and $E_2$ at the lower part of FIG. 1 represent E image information corresponding to patient motion phases 0, 1 and 2, respectively. This image information can be obtained by reconstruction of information obtained by E gated-acquisition. Here, information obtained in E gated-acquisition is the first detection information containing time information, to be described later, and patient motion phase information provided with time information. Because the T image information, $T_0$, $T_1$ and $T_2$ are morphological information, contours of a bone and internal organs are vivid, while because the E image information, $E_0$, $E_1$ and $E_2$ are functional information, contours thereof are not vivid. In FIG. 1, the contour of T image information is shown by a solid line, and the contour of E image information by a dotted line.

As a γ-ray source, there is used a radiation source emitting γ-ray radiation with energy difference from energy of γ-ray radiation being generated in a patient body by positron annihilation, and a radiation detector with good energy resolution such as a semiconductor radiation detector is used. Because of discrimination, based on energy of radiation detection signals, which are output from the radiation detectors, E measurement and T measurement can be executed in parallel. Each of the discriminated data obtained by these measurements (the first packet information and the second packet information to be described later) is divided for each patient motion phase, based on patient motion phase information obtained similarly as in known gated-acquisition. By using each of the divided data, each of E image information and T image information for each patient motion phase are reconstructed. In this way, the T image information, $T_0$, $T_1$ and $T_2$, and the E image information, $E_0$, $E_1$ and $E_2$, can be obtained.

T gated-acquisition generally requires a very long time, although it depends on the number of patient motion phases to be divided. However, by intentionally shifting the relation between the period of patient motion phase and the rotation period of the γ-ray source, gated-acquisition in a short time is possible also in T measurement. In a simulation by the inventors, such a result is obtained that when the number of patient motion phases per one respiration period is 8, and for example, the rotation period of the γ-ray source is (integer±0.1) times the respiration period of a patient, T measurement data satisfying reconstruction conditions can be obtained in about 10 minutes at the most, in the case where bed position is determined at a certain one position.

Each of the E image information and T image information obtained for each patient motion phase, by E gated-acquisition, and T gated-acquisition where the relation between the period of patient motion phase and the rotation period of the γ-ray source is intentionally shifted, is image information obtained in the case where these measurements are executed in parallel (at the same time) for the same moiety (for example, a moiety receiving impact of patient motion) of the same patient. There is no essential morphological difference of the patient, between the E measurement and the T measurement executed in parallel. That is, spatial relative displacement between two E image information corresponding to two patient motion phases in the E gated-acquisition becomes the same as that between two T image information corresponding to these patient motion phases in the T gated-acquisition. For example, spatial relative displacement $[F_{10}]$ between E image information $E_0$ at patient motion phase $0$ (reference phase), and E image information $E_1$ at patient motion phase $1$, in the E gated-acquisition is the same as the deformation between T image information $T_0$ of the reference phase and T image information $T_1$ at the patient motion phase $1$. Accordingly, by determination of information of the relative displacement between two patient motion phases in T gated-acquisition (for example, $[F_{10}]$ or $[F_{20}]$), and by applying the information of this relative displacement to two E image information at the two patient motion phases, non-linear superimposing of E image information at one patient motion phase, on E image information at the other patient motion phase (for example, reference phase) is possible. As a result, emission superimposed image information with non-linear superimposition can be obtained.

It should be noted that because T image information enables acquisition of morphological information of such as a body contour, a lung field and a bone, by using non-linear superimposition technology described in, for example, IEEE Transactions on Medical Imaging, Vol. 18, No. 8, pages 712 to 720, it is possible to superimpose T image information at each patient motion phase, on image of a reference phase, under non-linear strain.

FIG. 1 shows a process for obtaining emission superimposed image information. In FIG. 1, a respiration phase corresponding to an exhalation state of a patient is used as a reference phase, and T image information at that phase is used as reference image information $T_0$. When, onto this reference image information $T_0$, T image information $T_j$ at another respiration phase (it is assumed to be a phase j) is spatially superimposed, T image information $T_j$, which is superimposed on reference image information $T_0$, can be expressed as a mapping function like the following equation (for an explanation purpose, the number of phases to be divided is set as 3):

$$T_{jo}=[F_{jo}]\cdot T_j\ (j=1,2) \quad (1)$$

wherein $[F_{jo}]$ is a conversion matrix representing relative displacement from T image information $T_j$ corresponding to a respiration phase j to reference image information $T_0$. $T_{jo}$ at the left-hand side is T image information obtained by mapping T image information $T_j$ at a phase j on morphology at a patient body of a reference phase (reference image information $T_0$). Each of this plurality of T image information is expressed as a vector. It should be noted that it is easy to extract and store spatial mapping as a mapping function from a superimposing process.

Superimposition (mapping) of E image information (having ambiguous morphology) $E_j$ corresponding to a respiration phase j on reference image information $E_0$ is executed by using the conversion matrix $F_{jo}$ obtained from superimpose of the above T image information on E image information $E_j$. E image information $E_j$, which is superimposed on reference image information $E_0$, is a mapping represented by the equation (2). Reference image information $E_0$ is E image information corresponding to a reference phase.

$$E_{jo}=[F_{jo}]\cdot E_j\ (j=1,2) \quad (2)$$

As described above, after superimposing each of E image information at all patient motion phases other than a reference phase on reference E image information at a reference phase, each pixel value of each E image information is added to the pixel value of the reference E image information. By this processing, E image information $E_0'$ with high statistical accuracy, for patient morphology at a reference phase can be obtained. This is expressed by the equation (3).

$$E_0'=(E_0+E_{10}+E_{20})/3 \quad (3)$$

$E_{10}$ of the equation (3) represents the calculated value when j in the equation (2) is 1, and $E_{20}$ represents the calculated value when j in the equation (2) is 2.

By non-linear superimposition of corresponding E image information at a patient motion phase, based on relative displacement between corresponding T image information at two patient motion phases as described above, problems other than the above-described problem (5) can be improved. The problem (5), that is, a problem caused by morphological mismatching in attenuation compensation, can be solved by projection calculation based on these T image information, or by attenuation compensation using measurement data (projection data) used in reconstruction of T image information, because T image information having coincident morphology with E image information for each patient motion phase can be obtained.

The above-described respiratory motion compensation method (a patient motion compensation method) is calculated and processed by a patient motion compensation device 38 of FIG. 3, to be described later. Based on relative displacement between T image information at a certain two patient motion phases, image information superimposed with the E image information corresponding to the patient motion phases thereof is output to a display device 33, or output to a storage device 35 for display processing, etc., by still more superimposing other display information, and recorded.

Embodiment 2

Figure 2:
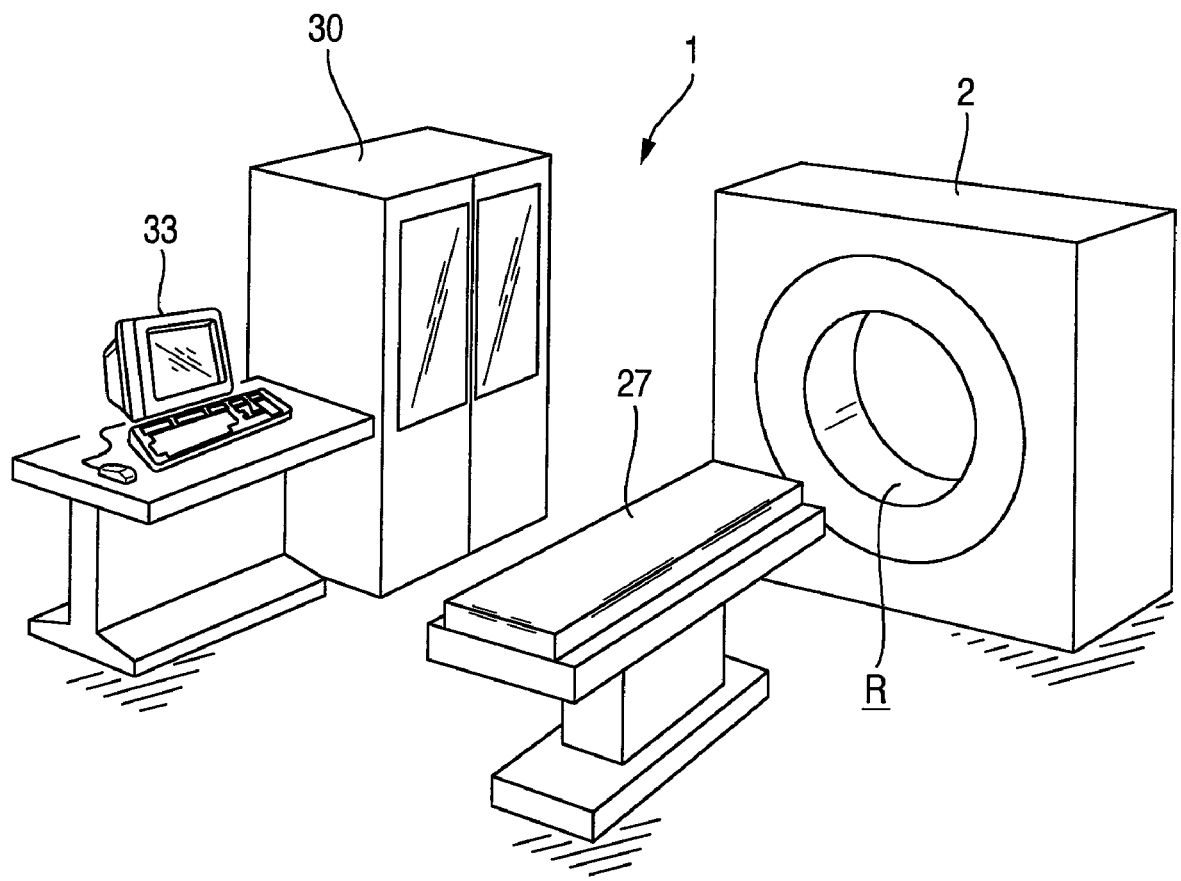
FIG. 2 is a schematic configuration drawing of a positron emission computed tomography device of one embodiment.

Explanation will be given of a positron emission computed tomography device 1 (the PET device), which is one suitable embodiment of the present invention, with reference to FIG. 2 to FIG. 7. FIG. 2 is a schematic configuration drawing of a positron emission computed tomography device of one embodiment. The PET device of the present embodiment, as shown in FIG. 2, has been provided with a computed tomography device 2, a bed 27 for supporting a patient 29, a data processing device 30 and a display device 33.

Figure 3:
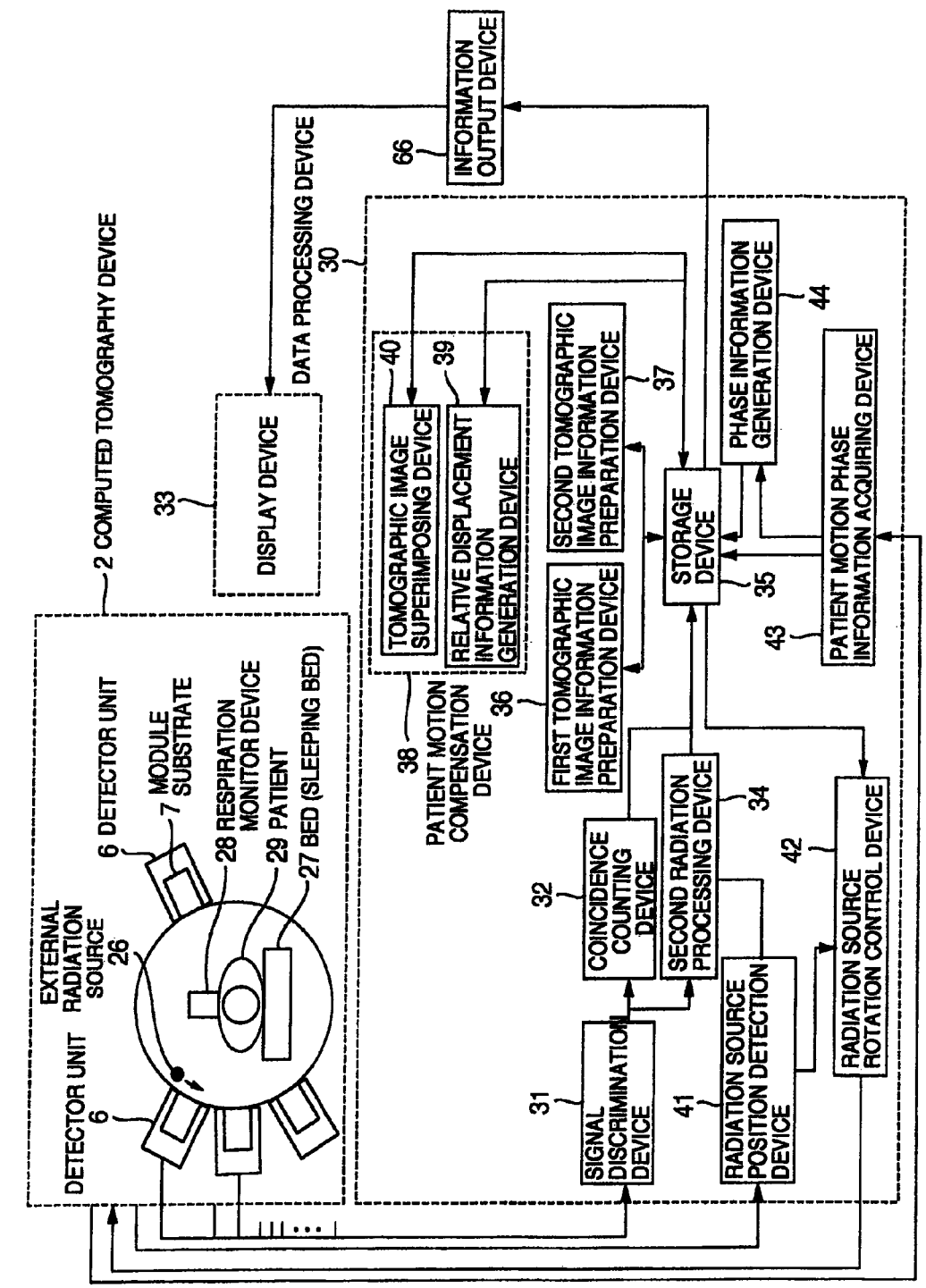
FIG. 3 is a detailed configuration drawing of a positron emission computed tomography device shown in FIG. 2.
Figure 4:
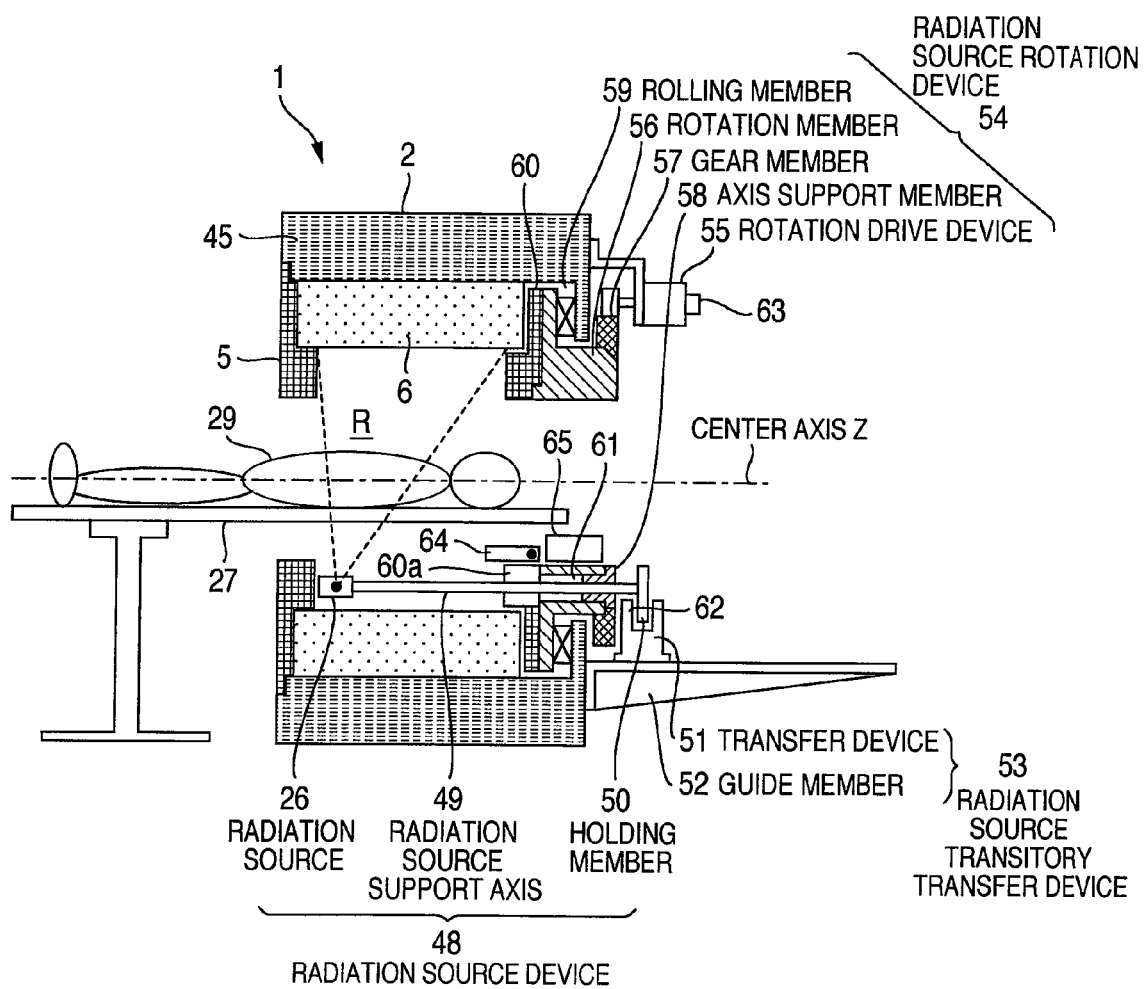
FIG. 4 is a longitudinal cross-sectional view of a computed tomography device shown in FIG. 1.
Figure 5:
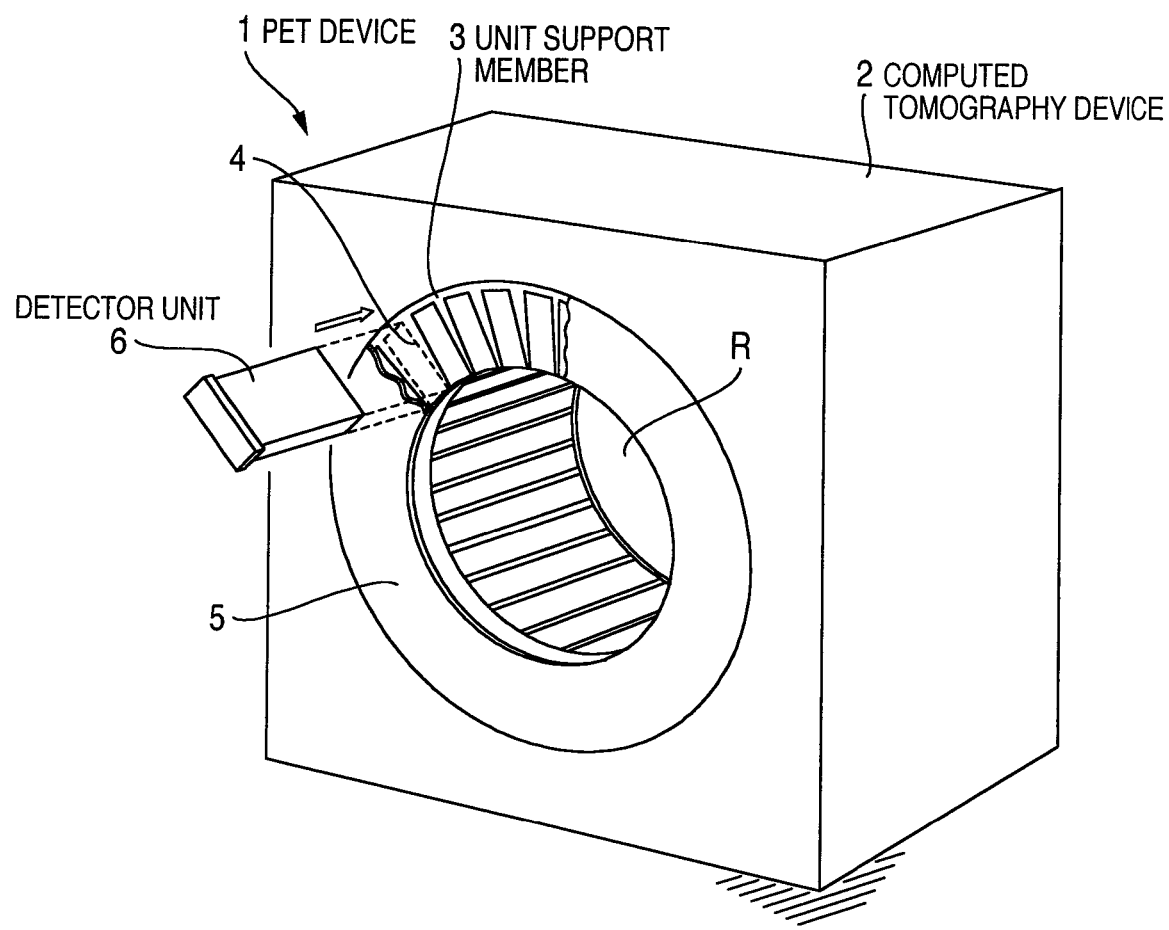
FIG. 5 is an explanation drawing of an installment state of detector units onto a computed tomography device.

The computed tomography device 2 has a housing 45 (refer to FIG. 4) encompassing a measurement space R, and a plurality of detector units 6 arranged so as to encompass the measurement space R (refer to FIG. 3 and FIG. 4). These detector units 6 are held by a unit support member 3 (refer to FIG. 5) installed at the housing 45 arranged by encompassing the measurement space R. These detector units 6 are inserted inside a plurality of opening parts 4 installed at the unit support member 3 and arranged in a circumference direction. After mounting the detector units 6 inside the opening parts 4, a ring-like front surface end shield 5 is attached at the housing 45 so as to cover the front surface of the detector units 6.

Figure 6:
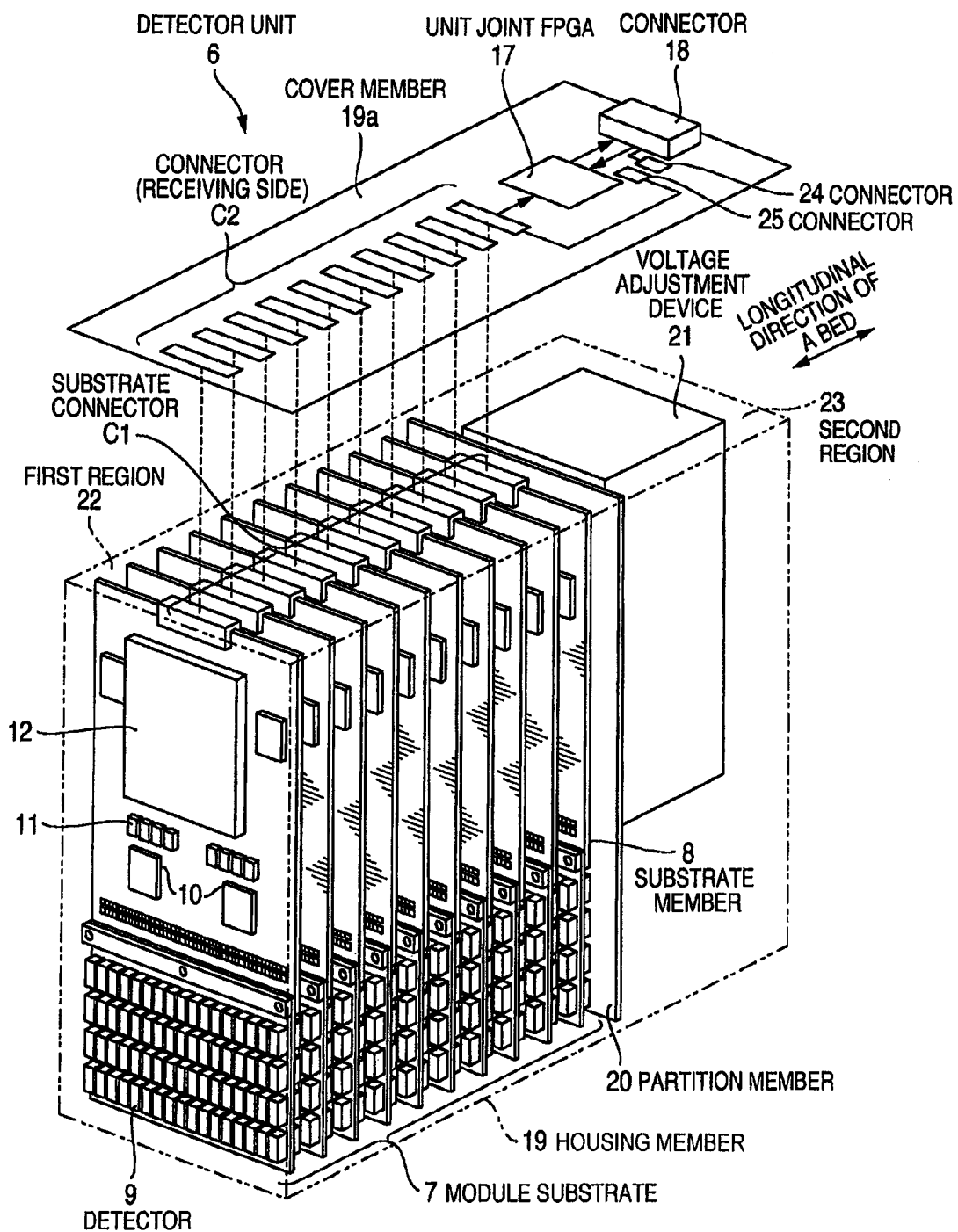
FIG. 6 is a perspective view showing a detailed configuration of the detector unit shown in FIG. 3.

FIG. 6 is a perspective view showing a detailed configuration of the detector unit. The detector units 6 have a housing member 19 formed with inside space and which has a rectangular shape, a plurality of semiconductor radiation detectors (hereafter called detectors 9) arranged inside the housing member 19, a plurality of Analog ASICs 10 and digital ASICs 12, which are signal processing devices, and a voltage adjustment device 21. The ASIC (Application Specific Integral Circuit) is an IC for specific applications. A plurality of detectors 9, a plurality of analog ASICs 10, a plurality of digital ASICs 12 and an analog to digital converter (an ADC 11) for converting an analog signal to a digital signal are attached at a substrate member 8. One sheet of a module substrate 7 has a plurality of detectors 9, a plurality of analog ASICs 10 and digital ASICs 12, and the substrate member 8. Space inside the housing member 19 is partitioned into a first region 22 and a second region 23 by a partition member 20 arranged inside thereof. A plurality of module substrates 7 are arranged inside the first region 22, and attached detachably at the housing member 19. These module substrates 7 have each substrate surface thereof arranged in a longitudinal direction of the housing member 19, that is in a longitudinal direction of the bed 27 (in a direction of a patient body axis), and arranged in parallel in a longitudinal direction thereof. The voltage adjustment device 21 is arranged inside the second region 23, and attached to the housing member 19.

Each detector 9 uses cadmium telluride (CdTe) as a semiconductor element part excellent in energy resolution. It is also possible to use cadmium zinc telluride (CZT), lead iodide ($PbI_2$), thallium bromide (TlBr) and gallium arsenide (GaAs), as the semiconductor element part. Each detector 9 detects γ-ray radiation of 511 keV (the first γ-ray) emitted from the patient 29 caused by the PET pharmaceutical, and γ-ray radiation (the second γ-ray) emitted from a γ-ray source (refer to FIG. 3 and FIG. 4), which is a radiation source 26 to be described later, and transmitted through the patient 29. These detectors 9 are positioned at nearer the measurement space R side than the analog ASICs 10 and the digital ASIC 12. The housing member 19 containing a cover member 19a is composed of a material having light shielding property such as aluminum and an aluminum alloy or the like.

The cover member 19a, which is a part of the housing member 19, is attached at one end part of the housing member 19 detachably. A unit joint FPGA (Field Programmable Gate Array, hereafter called a FPGA 17), and connectors 18, 24, 25 and C2 are installed at the cover member 19a. Signal wirings (not shown) of a plurality of connectors C2 are connected to the FPGA 17, and power source wirings (not shown) of these connectors C2 are connected to the connector 25. A signal wiring (not shown) of the connector 18 is connected to the FPGA 17, and a power source wiring (not shown) of the connector 18 is connected to the connector 24. The voltage adjustment device 21 is connected to the connector 24 and the connector 25.

FIG. 7 is a perspective view showing a detailed configuration of a module substrate. The analog ASICs 10, the analog to digital converter (ADC 11), the digital ASIC 12 and a connector C1 are connected by the signal wirings in this order.

One analog ASIC 10 is provided with a plurality of analog signal processing circuits (analog signal processing devices) 10a. The analog signal processing circuit 10a having a fast system and a slow system is installed by each detector 9. The fast system has a timing pick-off circuit 10b for outputting a timing signal for specifying detection time of γ-ray. The slow system is connected with and installed with a polar amplifier (a linear amplifier) 10d, a band-pass-filter (a waveform fixing device) 10e, and a peak-hold circuit (wave height value holding device) 10f, in this order. The analog signal processing circuit 10a has a charge amplifier (preamplifier) 10c connected to the timing pick-off circuit 10b and the polar amplifier 10d. The charge amplifier 10c is connected to one detector 9.

A digital ASIC 12 has, as shown in FIG. 7, a plurality of packet data generation devices 13 containing a plurality of time determination circuits (time information generation devices) 14 and one packet data generator 15, and a data transfer circuit (data sending device) 16, and having all these in an LSI configuration. All of the digital ASICs 12 installed at the positron emission computed tomography device 1 receive an input clock signal from a clock generation device (not shown) of 500 MHz, and are operated in synchronization. The clock signal input to the digital ASIC 12 is input to each of the time determination circuits 14 inside the packet data generation device 13. Each of the time determination circuits 14 inside the packet data generation device 13 is connected to the timing pick-off circuit 10b inside the separate analog signal processing circuit 10a.

The detector 9, which detected an incident γ-ray, outputs a γ-ray detection signal. The detector 9 outputs the first γ-ray detection signal, when the γ-ray is the first γ-ray, and outputs the second γ-ray detection signal, when the γ-ray is the second γ-ray. In the case of describing hereafter simply as γ-ray without differentiating the first γ-ray and the second γ-ray, it means both of the γ-rays, and in the case of describing simply as a γ-ray detection signal without differentiating the first γ-ray detection signal and the second γ-ray detection signal, it means both of the γ-ray detection signals. The γ-ray detection signal, which is output from the detector 9, is amplified with the charge amplifier 10c and the polar amplifier 10d. The amplified γ-ray detection signal is input to the peak-hold circuit 10f via the band-pass-filter 10e. The peak-hold circuit 10f holds wave height value of the γ-ray detection signal.

The wave height value signal, which is output from the peak-hold circuit 10f, is input to the packet data generator 15 by being converted to a digital signal with the ADC 11. The timing pick-off circuit 10b receives input of the γ-ray detection signal amplified by the charge amplifier 10c, and outputs a timing signal showing detection timing of a γ-ray. This timing signal is input to the corresponding time determination circuit 14. The time determination circuit 14 determines detection time of a γ-ray, based on a clock signal in receiving an input timing signal, and outputs detection time information.

The packet data generator 15, when it receives input information of detection timing, specifies the detector ID of the detector 9 corresponding to the time determination circuit 14, which output the detection time information. The packet data generator 15 generates packet information, which is digital information containing detection time information, detector ID information (detector position information) and wave height value information (energy information of the γ-ray detection signal), corresponding to one detector 9. This packet information is input to the data transfer circuit 16. A signal wiring (not shown) connected to the data transfer circuit 16 is connected to a signal wiring connected to the connector C2 via the connector C1. It should be noted that the electric power wiring connected to the connector C2 is connected to the electric source wiring (not shown) connected to the connector C1. The latter electric power wiring is connected to each element installed at the module substrate 7 such as detector 9 and the timing pick-off circuit 10b, arranged inside the substrate member 8.

The data transfer circuit 16 of each module substrate 7 arranged inside one detector unit 6 outputs packet information to the FPGA 17 of the detector unit 6. Each packet information, which is output from each FPGA 17 of all detector units 6 installed at the computed tomography device 2, is sent to a signal discrimination device 31 of the data processing device 30 via an information transfer wiring (not shown) connected to each connector 18.

FIG. 4 is a longitudinal cross-sectional view of a computed tomography device. The computed tomography device 2 is, as shown in FIG. 4, still more provided with a γ-ray source device (a radiation source device 48), a radiation source rotation device 54 and a radiation source linear transfer device 53. A ring-like rear surface end shield 60 is attached at a rotation member 56 to be described later. The detector unit 6 is arranged between the front surface end shield 5 and the rear surface end shield 60, in an axial direction of the computed tomography device 2. The front surface end shield 5 and the rear surface end shield 60 are radiation shielding bodies.

The radiation source rotation device 54 has a rotation drive device 55 (for example, a motor), the rotation member 56, a ring-like gear member 57, an axis support member 58 and a rolling member 59. The rotation member 56 is arranged at the rear end part of the housing 45. A part of the rotation member 56 is arranged between the housing 45 and the rear surface end shield 60, and is attached at the rolling member 59 (for example, a thrust bearing) attached at the housing 45. The rolling member 59 supports the rotation member 56. The rotation drive device 55 is attached at the housing 45. The rolling member 59 supports the rotation member 56. The rotation drive device 55 is attached at the housing 45. A gear installed at the rotation axis of the rotation drive device 55 is engaged with the gear member 57 installed at the rotation member 56 encompassing a circumference part of the rotation member 56. The rear surface end shield 60 rotates with the rotation member 56. An encoder 63 attached at the rotation drive device 55 is jointed to the rotation axis of the rotation drive device 55.

A radiation source device 48 has a radiation source 26, which is a γ-ray source, a radiation source support axis 49 and a holding member 50. The radiation source 26 is attached at one end of the radiation source support axis 49, and the holding member 50 is attached at the other end of the radiation source support axis 49. The radiation source support axis 49 is arranged so as to be parallel to the center axis (the center axis of the measurement space R) Z of the computed tomography device 2. The radiation source 26 is arranged at nearer position to the Z side than the detector unit 6, that is, between the detector unit 6 and the bed 27. The radiation source support axis 49 penetrates the axis support member 58 installed at the rotation member 56. The axis support member 58 is a radiation shielding body and shields one end part of the radiation source storage chamber 61 formed inside the rotation member 56. A notch part 60a for the radiation source 26, stored in the radiation source storage chamber 61, to pass through is installed at the rear surface end shield 60. Radiation source shields 64 and 65, which are radiation shielding bodies, are installed. The radiation source shield 64 is arranged facing to the notch part 60a, and the radiation source shield 65 is arranged facing to the position of the radiation source storage chamber 61.

The radiation source 26 is provided with a radioisotope, which emits the second γ-ray with energy different from that of the first γ-ray. As this radio isotope, cesium 137 emitting a γ-ray of 662 keV is used. Instead of cesium 137, cobalt 57 (emitting the second γ-ray of 122 keV), technetium 99m (emitting the second γ-ray of 140 keV), tellurium 123m (emitting the second γ-ray of 159 keV), cerium 139 (emitting the second γ-ray of 166 keV), gadolinium 153 (emitting the second γ-ray of 153 keV) and americium 241 (emitting the second γ-ray of 57 keV), etc. may also be used. An X-ray source, etc. as another radiation source, may also be used.

The radiation source transitory transfer device 53 is provided with a transfer device 51 and a guide member 52. The guide member 52 extends in an axial direction of the computed tomography device 2, and is attached at the side surface of the rear end of the housing 45. The transfer device 51 moves along the guide member 52 in the axis direction thereof, and has a channel 62 inserted with the holding member 50. The transfer device 51 enables movement in the axis direction thereof, in a state that the radiation source 26 is present at the lowest position, that is, in a state that the holding member 50 is inside the channel 62. By movement of the transfer device 51, the radiation source 26 is moved between the front surface end shield 5 and the axis support member 58 in the axis direction of the computed tomography device 2. The radiation source 26 is stored in the radiation source storage chamber, when T measurement is not executed. When T measurement is executed, the channel 62 is drawn out from the holding member 50, by driving the rotation drive device 55 and rotating the rotation member 56, and the radiation source 26 is rotated around the patient 29 lying on the bed 27.

FIG. 3 is a detailed configuration drawing of a positron emission computed tomography device shown in FIG. 2. A data processing device 30, as shown in FIG. 3, is provided with a signal discrimination device 31, a coincidence counting device 32, a second radiation processing device 34 (a transmission data processing device), a first tomographic image preparation device 36 (an emission image information preparation device), a second tomographic image preparation device 37 (a transmission image information preparation device), a patient motion compensation device 38, a radiation source position detection device 41, a radiation source rotation control device 42, a patient motion phase information acquiring device 43, a phase information generation device 44 and a storage device 35. These devices are composed of a computer and a circuit substrate and the like. The patient motion compensation device 38 contains relative displacement information generation device 39 and a tomographic image superimposing device 40.

The signal discrimination device 31 is connected to each connector 18 of each detector unit 6, and still more connected to each of the coincidence counting device 32 and the second radiation processing device 34. The radiation source position detection device 41 is connected to each of the encoder 63, the second radiation processing device 34 and the radiation source rotation control device 42. The radiation source rotation control device 42 controls drive of the rotation drive device 55. The storage device 35 is connected to each of the coincidence counting device 32, the second radiation processing device 34, the patient motion phase information acquiring device 43, the phase information generation device 44, the first tomographic image preparation device 36, the second tomographic image preparation device 37, the relative displacement information generation device 39, the tomographic image superimposing device 40 and an information output device 66. The relative displacement information generation device 39 is connected to the tomographic image superimposing device 40. The patient motion phase information acquiring device 43 is connected to a respiration monitor device 28.

The respiration monitor device 28 is a device for monitoring breath temperature of the patient 29, and is mounted on the face of the patient 29. The patient motion phase information acquiring device 43 receives input of breath temperature information measured with the respiration monitor device 28, and determines an interval, as a respiration period, between change timings from exhalation to inhalation, and between peaks when breath temperature becomes highest. As the respiration monitor device, there may be used an infrared camera or an optical stereo camera, for measuring displacement of the chest part surface skin of the patient 29. In using the infrared camera or the optical stereo camera, the relevant camera, which is installed on a supporting member such as a tripod, is arranged at a position making possible photographing of the patient 29 at the vicinity of the computed tomography device 2. In this case, the patient motion phase information acquiring device 43 analyzes a displacement waveform of the chest part surface skin, based on picture information, which is input from the infrared camera or the optical stereo camera, and determines a respiration period. Alternatively, a device enabling respiration monitor is separately prepared, and a signal, which is output from this device and gives a clue of phase information analysis, may be input to the patient motion phase information acquiring device 43.

Explanation will be given in detail of the PET inspection using the PET device of the present embodiment, and on preparation of image information, based on information obtained by this inspection.

An operator (a doctor or a radiation engineer) inputs information necessary to the PET inspection from an input device (not shown) installed at an operator console (not shown). This input information contains information relating to the patient 29 and the PET pharmaceutical, and still more information for respiratory motion compensation. For example, information for respiratory motion compensation includes 12 minutes, which is PET inspection time, and 8, which is number of patient motion phases per one respiration phase. The operator still more inputs an inspection start order from the input device. A bed drive device (not shown), which received input of this inspection start order moves the bed 27, on which the patient 29 is lying, who was administered with the PET pharmaceutical, in a longitudinal direction thereof, and inserts the patient 29 inside the measurement space R. The patient 29 is positioned at a predetermined position of the axis direction inside the measurement space R.

The respiration monitor device 28, which received input of this inspection start order, starts monitoring of respiration of the patient 29. The patient motion phase information acquiring device 43 determines respiration period, as described above, based on measurement information of the respiration monitor device 28, that is, temperature measurement value of breath of the patient 29. The patient motion phase information acquiring device 43 orders the storage device 35 to store respiration waveform information of each respiration period determined. The information output device 66 outputs the respiration waveform information for each respiration period of the patient 29, which was read out from the storage device 35, onto the display device 33. The output of relating information onto the display device 33 by the information output device 66 is executed by a request order from the operator, which is input from the above input device. When the respiration waveform information of the patient 29, which is displayed on the display device 33, is stabilized, the operator inputs a T measurement start order to the input device so as to start T measurement. The respiration waveform information stabilizes in several minutes. The T measurement is executed in parallel to E measurement within a period where E measurement is executed.

The T measurement start order is input from the input device to each of the phase information generation devices 44, the radiation source linear transfer control device (not shown) and the radiation source rotation control device 42.

The phase information generation device 44, which received input of the T measurement start order, divides the respiration waveform information of each respiration period by a time axis, based on the respiration waveform information for each respiration period, which is input from the patient motion phase information acquiring device 43, and the number of patient motion phases (for example, 8) in one respiration period, which is input by the operator from the above input device. The phase information generation device 44 provides time information by each divided patient motion phase. In providing this time information, the start time of a respiration period and the detection time of a γ-ray, which is determined by the time determination circuit 14, may be mismatched unless being synchronized, and gives a trouble in preparation of E image information and T image information at each patient motion phase, by the first tomographic image preparation device 36 and second tomographic image preparation device 37. Explanation will be given of a method for synchronizing E gated-acquisition and T gated-acquisition. A packet containing time information is sent from the detector unit 6 to the data processing device 30. The patient motion phase information acquiring device 43 acquires the packet containing time information in real time, via the storage device 35. The phase information generation device 44 obtains time information from the patient motion phase information acquiring device 43. For example, in the case where the respiration period determined is 4 seconds, because the patient motion phase function thereof is 8, which was input from the input device, the time width of one patient motion phase becomes 0.5 second. Time information is provided for each of 8 patient motion phases, each divided into 0.5 second. This processing is repeated for each respiration period. In addition to uniform division of respiration period, in the case where the displacement of an up-down motion of the chest part skin surface of the patient 29 was determined, based on a picture of an infrared camera, patient motion phase may be divided by using indices of waveform and displacement amount of the displacement of the up-down motion. Information on each patient motion phase, provided with time information by each respiration period, is stored in the storage device 35.

A control device for controlling the radiation source transitory transfer device 53, which received input of the T measurement start order, outputs a drive order to the transfer device 51. The radiation source support axis 49 engaged with the transfer device 51 moves toward the front surface end shield 5. By this movement, the radiation source 26 moves from the radiation source storage chamber 61 to the outside, and is set at predetermined position between the front surface end shield 5 and the rear surface end shield 60.

The radiation source rotation control device 42 determines a rotation period and a rotation number of the radiation source 26 suitable to execute T gated-acquisition in a short time, by using information on the respiration period and information on each of the divided patient motion phases, which are stored in the storage device 35. The radiation source rotation control device 42, which received input of the T measurement start order, controls rotation of the rotation drive device 55 so as to attain the rotation period and the rotation number determined, after the radiation source 26 is set at the above predetermined position. For example, in the case where the respiration period of a patient is 4 seconds, the radiation source 26 is rotated around the patient 29 for about 12 minutes, in a period of 16.4 seconds, that is 4.1 times thereof. Rotation force of the rotation drive device 55 is conveyed to the rotation member 56 via the gear member 57 to rotate the rotation member 56. The radiation source 26 rotates with the rotation member 56, and rotates around the patient 29. The second γ-ray radiation of 662 keV emitted from the radiation source 26 is irradiated onto the patient 29 on the bed 27 from the circumference, accompanying with rotation of the radiation source 26. T measurement is executed under rotation of the radiation source 26.

For example, when rotation of the radiation source 26 is started, the operator inputs a data collection start order to the above input device. When this data collection start order is input to the signal discrimination device 31, the signal discrimination device 31 starts input of each packet information, which was output from each detector unit 6.

Explanation will be given of the generation of packet information in each of the E measurement and T measurement, which is input to the signal discrimination device 31.

During a period when the patient 29 is inserted in the measurement space R, all of the detectors 9 encompass the patient 29. In this state, E measurement is executed. Pair γ-rays (a pair of the first γ-rays) generated in annihilation of a positron, which was generated caused by the PET pharmaceutical accumulated at an affected part of a malignant tumor, is injected into a pair of the detectors 9, which are located in about a 180 degree opposite direction of the computed tomography device 2, and detected by these detectors 9. The detector 9, which has detected the first γ-ray, outputs the first γ-ray detection signal. The timing pick-off circuit 10b of the analog signal processing circuit 10a, which receives input of this first γ-ray detection signal, outputs a timing signal, and the peak-hold circuit 10f outputs a wave height value signal. The time determination circuit 14, which receives input of this timing signal, generates detection time information of the first γ-ray, which is determined based on the timing signal, as described above. The packet data generator 15, which received input of the wave height value information and the detection time information, which were converted to digital signals by ADC 11, generates packet information for the detected first γ-ray (hereafter called the first packet information). This first packet information contains detection time information, detector ID information and wave height value information, for the first γ-ray. The first packet information obtained by E measurement is input to the signal discrimination device 31.

In T measurement, the second γ-ray emitted from the radiation source 26 and transmitted through the patient 29 is detected with the detector 9. The second γ-ray detection signal, output from the detector 9, which detected the second γ-ray, is processed by the analog signal processing circuit 10a and the packet data generation device 13, similarly as in the first γ-ray detection signal. The packet data generator 15 generates packet information for the detected second γ-ray (hereafter called the second packet information). This second packet information contains detection time information, detector ID information and wave height value information for the second γ-ray. The second packet information obtained by E measurement is also input to the signal discrimination device 31.

In terminating T measurement, the operator inputs a T measurement termination order from the above input device. The radiation source rotation control device 42, which received input of the T measurement termination order, outputs a stop control order to the rotation drive device 55, and stops the rotation drive device 55, when the radiation source 26, which is a γ-ray source, has reached the lowest position. In this state, the holding member 50 is located inside the channel 62 of the transfer device 51. The radiation source linear transfer control device, which received input of the T measurement termination order, controls the transfer device 51, so as to move apart from the housing 45. Because the transfer device 51 moves so as to be apart from the housing 45, the radiation source 26, which is a γ-ray source, is stored inside the radiation source storage chamber 61, and irradiation of the second γ-ray radiation onto the patient 29 is stopped.

After input of the data collection start order, the signal discrimination device 31 receives both inputs of the first packet information and the second packet information, which were output from each detector unit 6, because E measurement and T measurement are executed in parallel, and discriminates these packet information, based on energy of detected γ-ray, that is wave height value information. The signal discrimination device 31 outputs the first packet information, containing the wave height value information corresponding to energy of the first γ-ray, that is, the wave height value information in a range corresponding to an energy of, for example, 450 to 550 keV, to the coincidence counting device 32. The second packet information, containing the wave height value information corresponding to energy of the second γ-ray, that is, the wave height value information in a range corresponding to an energy of, for example, 570 to 650 keV, is output to the second radiation processing device 34. Exchange of output destination of these packet information is executed by exchanging an exchange switch (not shown) installed inside the signal discrimination device 31.

The coincidence counting device 32 executes coincidence counting by using detection time information and detector ID, obtained based on the first γ-ray detection signal, and specifies a pair of the detectors 9, which detected a pair of the first γ-rays generated by annihilation of one positron. The coincidence counting device 32 orders the storage device 35 to store each detector ID information and detection time information contained in the first packet information of a pair of the specified detectors 9. Each detector ID information and detection time information, obtained by coincidence counting, are called the first detection information.

The radiation source position detection device 41 receives input of an output signal (rotation angle information of the rotation drive device 55) of the encoder 63, and determines position information of the radiation source 26, which is rotating, based on this output signal (hereafter called radiation source position information). The radiation source position information is input to the radiation source rotation control device 42, and the second radiation processing device 34 as feed-back information.

The second radiation processing device 34 orders the storage device 35 to store detector ID information and detection time information of the detector 9, which detected the second γ-ray, contained in the second packet information, and additional radiation source position information. The detector ID information, detection time information, and radiation source position information, which are output from the second radiation processing device 34, are called the second detection information. Because the first detection information and the second detection information each contains detection time information, it contributes to correspond to patient motion phase information provided with time information, which is generated by the phase information generation device 44.

The second tomographic image preparation device 37 reconstructs T image information for each patient motion phase, by using the second detection information stored in the storage device 35, and patient motion phase information provided with time information. Specifically, the second tomographic image preparation device 37 prepares T image information for the above certain patient motion phase, by using time information at a certain patient motion phase, that is the second detection information having time information contained in between time information of this patient motion phase and time information of the next patient motion phase. This T image information is provided with corresponding patient motion phase time information, and stored by the storage device 35. In this way, T image information for each of the patient motion phases, 0, 1, 2, - - - 7, for example, T image information, $T_0, T_1, T_2, ---T_7$ (refer to FIG. 1) is prepared.

The first tomographic image preparation device 36 reconstructs E image information for each patient motion phase, by using the first detection information stored in the storage device 35, and patient motion phase information provided with time information. E image information for the above certain patient motion phase is prepared, by using the first detection information having time information contained in between time information of this patient motion phase and time information of the next patient motion phase. This E image information is provided with corresponding patient motion phase time information. This E image information is provided with time information of corresponding patient motion phase, and stored by the storage device 35. In this way, information for each of the patient motion phases, 0, 1, 2, - - - 7, for example, E image information, $E_0, E_1, E_2, ---E_7$ (refer to FIG. 1) is prepared.

In reconstruction of E image information at a certain patient motion phase, attenuation compensation for the first detection information is executed, based on the second detection information at that patient motion phase, or a tomographic image relating to a transmittance of the second γ-ray, reconstructed at that patient motion phase, and E image information is reconstructed. Here, the tomographic image relating to the transmittance of the second γ-ray corresponds to T image information at a patient motion phase.

The first tomographic image preparation device 36 and the second tomographic image preparation device 37 prepare E image information and T image information for each patient motion phase, respectively, by using a tomographic image reconstruction algorithm, for example, a filtered-back-projection method, etc. Each of E image information and T image information is a tomographic image information, and is prepared for each 8 sets for each respiration period. The first tomographic image preparation device 36 executes attenuation compensation. In the case where attenuation compensation is necessary, it is executed from T image information at the same patient motion phase for the first detection information, however, in the present embodiment, by parallel measurement (substantially coincidence counting) of T measurement and T measurement, morphological identity of the patient 29 is guaranteed. Therefore, in the present embodiment, artifact and deterioration of quantitativeness accompanied with position mismatch in E gated-acquisition and T gated-acquisition in attenuation compensation are far less as compared with conventional E gated-acquisition.

It should be noted that each E image information for each patient motion phase obtained at the stage before preparation of superimposed image information, based on E gated-acquisition, corresponds to measurement data at a divided period of total inspection time with number of patient motion phases. That is, when patient motion phases are divided equally with time, it is one reconstructed from measurement data of 8 division of 12 minutes, that is 1.5 minute per one patient motion phase. In the usual administration amount of the PET pharmaceutical, image information can be obtained, however, statistical accuracy is absolutely insufficient, and thus it is image information containing many noises. In conventional gated-acquisition, because of absence of a preparation step for superimposed image information, based on E gated-acquisition, to be described later, it is obtained only 8 image reconstructed from measurement data of substantially 1.5 minute. To obtain a clear image with low noise, measurement of equal to or longer than 3 minutes is generally required, therefore, a clear image cannot be obtained by conventional gated-acquisition.

Explanation will be given of specific processing for non-linear superimposing of T image information themselves and E image information themselves for each patient motion phase, described by using FIG. 1. This processing is executed by the patient motion compensation device 38. The relative displacement information generation device 39 acquires each T image information provided with time information at a patient motion phase stored in the storage device 35 (for example, in the case where 8 patient motion phases are present in one respiration period, T image information, $T_0, T_1, T_2, ---, T_7$), and each patient motion phase information provided with time information (for example, in the case where 8 patient motion phases are present in one respiration period, patient motion phases 0, 1, 2, - - - , 7). The relative displacement information generation device 39 superimposes T image information, $T_1, T_2, ---, T_7$, at each of patient motion phases 1 to 7 in a certain one respiration period, on T image information $T_0$ at a patient motion phase 0 (a reference phase) to prepare T superimposed image information for one respiration period. This non-linear superimposing processing of image information is executed by using an algorithm called a "Non-linear Image Registration Method" described in IEEE Transactions on Medical Imaging, Vol. 18, No. 8, pages 712 to 720. By superimposing of the T image information, each relative displacement information between T image information $T_0$ at a reference phase and each of T image information at each of other patient motion phases, that is, conversion matrix information $[F_{10}], [F_{20}], ---, [F_{70}]$, can be obtained. This relative displacement information is stored in the storage device 35.

The tomographic image superimposing device 40 receives input of each E image information provided with time information at a patient motion phase stored in the storage device 35 (for example, in the case where 8 patient motion phases are present in one respiration period, E image information, $E_0, E_1, E_2, ---, E_7$) and the above-described each patient motion phase information provided with time information. The tomographic image superimposing device 40 superimposes E image information, $E_1, E_2, ---, E_7$, at each of patient motion phases 1 to 7 in a certain one respiration period, on E image information $E_0$ at a patient motion phase 0 (a reference phase) non-linearly, by using a plurality of conversion matrix information $[F_{10}], [F_{20}], ---, [F_{70}]$, to prepare E superimposed image information for one respiration period. This non-linear superimposing processing of image information is executed by using the above-described algorithm called a "Non-rigid Image Registration Method". The tomographic image superimposing device 40 executes addition processing of pixel values of each pixel at the same spatial position, for all the pixels of E image information at the reference phase, by using each E image information at each patient motion phase. The resulting E superimposed image information is stored in the storage device 35. The above-described preparation process of E superimposed image information is executed for each respiration period within a period of the PET inspection.

The tomographic image superimposing device 40 still more executes addition processing of pixel values of each pixel at the same spatial position of E superimposed image information, for all the pixels of a certain one E superimposed image information, by using each E superimposed image information at the reference phase prepared at each respiration period. Statistical-noise-suppressed motion-compensated E image information, obtained by such addition of pixel values, becomes more vivid image information with high statistical accuracy. The statistical-noise-suppressed motion-compensated E image information is stored in the storage device 35.

The information output device 66 reads out, from the storage device 35, each T image information, and each E image information for each patient motion phase, each T superimposed image information, and each E superimposed image information for each respiratory period, and statistical-noise-suppressed motion-compensated T information, and statistical-noise-suppressed motion-compensated E information, each singly by image information, or together of a plurality kinds of image information, and outputs to the display device 33. The display device 33 displays image information, which was input. Image information displayed at the display device 33 is read out to the display device 33 by the information output device 66, based on an image information display order, which the operator inputs from the input device of the operator console.

In the present embodiment, by using relative displacement information, that is, conversion matrix information, obtained by superimposing, on T image information of a certain patient motion phase (for example, a reference phase), T image information of other patient motion phases, there is superimposed, on E image information at this one patient motion phase, E image information at the above other patient motion phases, therefore E image information at each of the patient motion phases in one respiration period can be superimposed all together. Accordingly, more vivid E image information (statistical-noise-suppressed motion-compensated image), with a target of a moiety receiving impact of patient motion (for example, respiratory motion), can be obtained in a shorter time. According to the more vivid E image information (statistical-noise-suppressed motion-compensated image), obtained by the present embodiment, diagnosis of a malignant tumor, present at a moiety receiving impact of patient motion, can be executed with good accuracy. Statistical accuracy, expected for this E image information in the present embodiment, corresponds to that in E measurement of 12 minutes. Usually, by execution of E measurement for 12 minutes, statistical accuracy can be satisfied sufficiently. In addition, this statistical-noise-suppressed motion-compensated image information is a vivid image with small blurring and high quantitativeness, because respiratory motion is also compensated for by each of the T image information at each of the patient motion phases in the present embodiment. In addition, because of no generation of position mismatch of the patient 29, in T measurement and E measurement in attenuation compensation, an artifact accompanying the position mismatch is also not generated. The patient 29 can continue respiration in a calm state, and is not required to hold his or her breath during the period of the PET inspection in the present embodiment.

As described above, the reason for being able to utilize relative displacement information obtained, based on T image information at a patient motion phase, in superimposing E image information at different patient motion phases is that E measurement and T measurement are executed in parallel, and the reason is owing to detection of the first γ-ray and the second γ-ray with one detector 9. In many cases, one detector 9 outputs the first γ-ray detection signal and the second γ-ray detection signal with time mismatch. The first packet information and the second packet information prepared based on these γ-ray detection signals can be discriminated easily by the signal discrimination device 31, based on the energy of the γ-ray detection signals. That is, because the signal discrimination device 31 receives input of wave height value corresponding to energy of the γ-ray detection signal obtained by the peak-hold circuit (a wave height value holding device) 10f, the first packet information and the second packet information obtained by the peak-hold circuit 10f for the determination can be classified easily.

If necessary, in adding pixel values of a set of E image information at other patient motion phases to pixel value of E image information at a reference phase, by execution of the addition processing, by adjusting the pixel values in consideration of a stretching and contracting degree of the E image information, which is deformed non-linearly, quantitativeness of the accumulation degree of the PET pharmaceutical can be enhanced still more.

On one or a plurality of display device 33 installed at the operator console, E image information and T image information at the same patient motion phase, or T superimposed image information and E superimposed image information at a reference phase can be displayed, along with statistical-noise-suppressed motion-compensated E image information. By such display, the statistical-noise-suppressed motion-compensated E image information can be evaluated.

As described above, in order to obtain more vivid emission image information in a short time, with a moiety receiving impact of patient motion as a target, there is executed a tomographic image information preparation method of a positron emission computed tomography device, wherein first image information is prepared at a plurality of phases obtained by dividing a certain period, in terms of time, based on a plurality of first information obtained by a plurality of first radiation detection signals, which are output from a plurality of radiation detectors surrounding a bed, when first radiation caused by a radiopharmaceutical is input; second tomographic image information is prepared at a plurality of phases, based on a plurality of second information obtained by a plurality of second radiation detection signals, which are output from a plurality of radiation detectors, when second radiation emitted from a radiation source is input; relative displacement information among a plurality of second tomographic image information is determined by superimposing, on the second tomographic image information at a certain one phase among a plurality of phases, a plurality of second tomographic image information at other phases; and superimposed first tomographic image information is prepared by superimposing, on the first tomographic image information at a certain one phase, a plurality of first tomographic image information at other phases, by using relative displacement information.

Description was given above of processing of superimposing, on T image information $T_0$ at a patient motion phase 0, T image information, $T_1, T_2, ---, T_7$, of other patient motion phases. However, the relative displacement information generation device 39 may execute similar superimposing processing of T image information and addition processing of pixel values, also in superimposing of each of T image information, $T_0, T_2, \text{---}, T_7$, at for example, patient motion phases, $0, 2, 3, \text{---}, 7$, on T image information of the patient motion phase 1, and addition of pixel values. Superimposing of other T image information on each of the residual T image information, $T_2, T_3, \text{---}, T_7$, and addition of pixel values are also executed similarly. T superimposed image information at each of patient motion phases, $0, 2, 3, \text{---}, 7$, provide image information with high statistical accuracy. By execution of attenuation compensation of E image information at a corresponding patient motion phase, by using this T superimposed image information, propagation of statistical noises contained in T image information in the attenuation compensation process to E image information can also be suppressed.

Still more, by interpolation in a time direction, by using both E image information of adjacent patient motion phases, vivid E image information for an arbitrary respiration phase can be obtained. By matching an arbitrary respiration phase to that of a breath-holding X-ray CT image of the same patient, which is imaged at a separate time, there can also be solved a problem of position mismatching between PET image and CT image, caused by a difference of a respiration state in E image information and X-ray CT image information. However, in this case, it is necessary to match a bed shape or a patient posture in advance.

The above-described embodiment used, as a target, gated-acquisition corresponding to respiratory motion, however, it is applicable also to gated-acquisition corresponding to heart beat.

It should be noted that in a nuclear medicine diagnosis device, there may be the case where energy is provided to a plurality of radiation detectors, due to scattering of γ-rays from the patient inside a certain radiation detector and absorbing by other radiation detectors. For such a case, it is considered to judge whether a γ-ray before being scattered is a γ-ray from the radiopharmaceutical administered to the patient P, based on radiation detection information by two or more radiation detectors, and if so, it is processed as an effective signal. Hereafter, such a method is called scattered ray processing. The nuclear medicine diagnosis device has a scattered light processing unit for specifying a plurality of radiation signals by radiation scattered by the radiation detector, as one radiation signal, based on output signals output from the radiation detectors. Here, the scattered light processing unit may be installed at the more upstream side of data processing than the signal discrimination device 31 of the 30. Because effective signals are increased by the scattered light processing, a diagnosis image with good accuracy can be expected.

It should be noted that, in the above embodiments, an example of a positron emission computed tomography device was shown, however, it may be an SPECT device, as long as it is capable of imaging a functional image of a living body. In addition, it is applicable not only to a two-dimensional tomographic image but also to the relation of a three-dimensional functional image and a structural image of a living body similarly. The above-described preparation method for image information may be applicable to an image taken by computer where a medical image receives impact of patient motion. That is, to obtain more vivid functional image information of a living body in a short time, with a moiety receiving impact of patient motion, as a target, there is executed an image information preparation method of an image processing device, wherein first image information is prepared, with function of a living body imaged at a plurality of phases obtained by dividing a certain period, in terms of time; second image information is prepared, with structure of a living body imaged at a plurality of phases; relative displacement information among the plurality of second image information is determined by superimposing, on the second image information at a certain one the phase among a plurality of phases, a plurality of second image information at other phases; and superimposed first image information is prepared by superimposing, on the first image information at a certain one the phase, a plurality of first image information at other phases, by using the relative displacement information.

It should be noted that in the above embodiments, a certain period of E image information and T image information was divided into 3 or 8, however, it may be divided into any specified number. In addition, an example of equal division of a period was shown, however, it may not be equal division, and the time of a certain division area may be set shorter or longer than the time of other division areas. For example, by setting the time shorter for an area receiving larger impact of patient motion and setting the time longer for an area receiving smaller impact of patient motion, image processing can be executed by differentiating the area receiving smaller impact of patient motion and the area receiving larger impact of patient motion, and a more vivid image can be obtained. In the case of setting the time shorter or longer for a certain division area as compared with another division area, by dividing with imaging time by added amount, instead of dividing with superimposed image number, 3, in the right-hand side of the equation (3), a superimposed image can be obtained.

As for divided areas, it is not necessary to use all of the areas in superimposition and a part of the areas may be specified and used in superimposition. For example, by specifying and superimposing an area including a time for complete air exhalation, which is an area with small impact of patient motion, and an area including a time for complete air inhalation, among all areas, an image with small impact of patient motion can be obtained and quick measurement is possible. In addition, by elimination of an image area with large impact of patient motion, and with an index expressing a blurring degree over predetermined value, image accuracy can be enhanced, while putting importance on quick measurement.

It should be noted that in the above embodiments, an example was given of synchronization of a patient motion period by imaging E image information, which is a functional image of a living body, and T image information, which is a structural image of a living body, by one imaging device, however, it is also possible to have synchronization of a patient motion period of a functional image of a living body, taken by a certain imaging device, and a structural image of a living body, taken by a separate imaging device. For example, by specifying a period of the functional image and a period of the structural image, and by assigning areas to be divided so that each of the starting points and the lengths of the periods are matched, synchronization of the functional image and the structural image can be obtained.

It should be further understood by those skilled in the art that although the foregoing description has been made on embodiments of the invention, the invention is not limited thereto and various changes and modifications may be made without departing from the spirit of the invention and the scope of the appended claims.

The invention claimed is:

1. An image information preparation method of an image processing device, the method comprising the steps of:
   preparing first image information, in which a function of a living body was imaged at a plurality of phases obtained by dividing a certain period in terms of time;
   preparing second image information, in which a structure of a living body was imaged at a plurality of said phases;

determining relative displacement information among the second image information thereof by superimposing, on said second image information at a certain one said phase among a plurality of said phases, said second image information at other said phases; and preparing superimposed first image information by superimposing, on said first image information at a certain one said phase, said first image information at other said phases, by using said relative displacement information.

2. A tomographic image information preparation method of a computed tomography device, wherein:

first tomographic image information is prepared at a plurality of phases obtained by dividing a certain period in terms of time, based on a plurality of first information obtained from a plurality of first radiation detection signals, which are output from a plurality of radiation detectors surrounding a bed, when a first radiation caused by a radiopharmaceutical is input;

second tomographic image information is prepared at a plurality of said phases, based on a plurality of second information obtained from a plurality of second radiation detection signals, which are output from a plurality of said radiation detectors, when a second radiation emitted from a radiation source is input;

relative displacement information among the second tomographic image information thereof is determined by superimposing, on said second tomographic image information at a certain one phase among a plurality of said phases, a plurality of said second tomographic image information at other said phases; and superimposed first tomographic image information is prepared by superimposing, on said first tomographic image information at said certain one said phase, a plurality of said first tomographic image information at said other said phases, by using said relative displacement information.

3. The tomographic image information preparation method of the computed tomography device according to claim 2, wherein:

said first information and said second information are discriminated by an energy difference between said first radiation detection signal and said second radiation detection signal;

said first tomographic image information is prepared by using said discriminated first information; and said second tomographic image information is prepared by using said discriminated second information.

4. The tomographic image information preparation method of the computed tomography device according to claim 2, wherein:

the relative displacement information among said second tomographic image information is non-linear relative displacement information; and said superimposed first tomographic information is prepared, by using said non-linear relative displacement information.

5. The tomographic image information preparation method of the computed tomography device according to claim 2, wherein:

preparation of said first tomographic image information at said phase is executed by attenuation compensation of said first information corresponding to said phase, by using said second tomographic image information at said phase.

6. The tomographic image information preparation method of the computed tomography device according to claim 2, wherein:

said first information comprises first detection time information of said first radiation;

said second information comprises second detection time information of said second radiation;

preparation of said first tomographic image information by each of said phases is executed by using said first information specified by said first detection time information; and preparation of said second tomographic image information by each of said phases is executed by using said second information specified by said second detection time information.

7. The tomographic image information preparation method of the computed tomography device according to claim 2, wherein:

a position of said radiation source in a rotating direction around said bed is detected, and a plurality of detected radiation source position information are used in preparation of said second tomographic image information.

8. The tomographic image information preparation method of the computed tomography device according to claim 2, wherein said radiation detector is a semiconductor radiation detector.

9. A tomographic image information preparation method of a computed tomography device, the method comprising the steps of:

generating a plurality of first information, which information comprise first detection time information of a first radiation, first position information of a radiation detector, from which a first radiation detection signal was output, and first energy information of said first radiation detection signal, obtained by a plurality of said first radiation detection signals, which are output from a plurality of said radiation detectors surrounding a bed, when said first radiation caused by a radiopharmaceutical is input;

specifying a pair of said radiation detectors which output said first radiation detection signal within a setting period, by execution of coincidence counting, based on said first detection time information contained in said plurality of first information;

preparing a plurality of first tomographic image information at a plurality of phases obtained by dividing a certain period in terms of time, based on said first position information and said first detection time information of a pair of said specified radiation detectors;

generating a plurality of second information, which information are obtained from a plurality of second radiation detection signals output from a plurality of said radiation detectors, when a second radiation emitted from a radiation source is input;

detecting a position of said radiation source in a rotation direction around said bed;

preparing a plurality of second tomographic image information at a plurality of said phases, based on a plurality of said second information and a plurality of said detected radiation source position information;

determining relative displacement information among the second tomographic image information thereof, by superimposing, on said second tomographic image information at a certain one phase among a plurality of said phases, a plurality of said second tomographic image information at other said phases; and preparing superimposed first tomographic image information by superimposing, on said first tomographic image information at a certain one said phase, a plurality of said first tomographic image information at other said phases.

10. The tomographic image information preparation method of the computed tomography device according to claim 9, wherein
said second information comprises the second detection time information of said second radiation, the second position information of said radiation detector, to which said second radiation detection signal was output, and a second energy information of said second radiation detection signal;
said first information and said second information are discriminated by said first energy information and said second energy information;
said coincidence counting is executed by using said first detection time information of said discriminated first information; and
preparation of said second tomographic image information is executed by using said discriminated second information.

11. A computed tomography device comprising:
a bed for supporting a patient;
a radiation source that rotates around said bed;
a plurality of radiation detectors, which are arranged around said bed, output a first radiation detection signal by detecting first radiation emitted from said patient, caused by a radiopharmaceutical, and output a second detection radiation signal by detecting the second radiation emitted from said radiation source;
a first tomographic image information preparation device, which prepares first tomographic image information at a plurality of patient motion phases obtained by dividing the patient motion period of said patient in terms of time, based on a plurality of first information obtained from a plurality of said first radiation detection signals;
a second tomographic image information preparation device, which prepares second tomographic image information at a plurality of said patient motion phases, based on a plurality of second information obtained from a plurality of second radiation detection signals;
a relative displacement information generation device, which determines the relative displacement information among the second tomographic image information thereof, by superimposing, on said second tomographic image information at a certain one said patient motion phase among a plurality of said patient motion phases, a plurality of said second tomographic image information at other said patient motion phases; and
a tomographic image information superimposing device, which prepares the superimposed first tomographic image information, by superimposing, on said first tomographic image information at a certain one said patient motion phase, said first tomographic image information at other said patient motion phases.

12. The computed tomography device according to claim 11, comprising a discrimination device, which receives input of said first information and said second information, and discriminates said first information and said second information, based on energy difference between said first radiation detection signal and said second radiation detection signal; wherein
said first tomographic image information preparation device prepares said first tomographic image information, by using said discriminated first information; and
said second tomographic image information preparation device prepares said second tomographic image information by using said discriminated said second information.

13. The computed tomography device according to claim 11, wherein said first tomographic image information preparation device executes preparation of said first tomographic image information at said patient motion phase, by execution of attenuation compensation of said first information corresponding to this patient motion phase, by using said second tomographic image information at said patient motion phase.

14. The computed tomography device according to claim 11, wherein
said first tomographic image information preparation device executes preparation of said first tomographic image information at each of said patient motion phases, by using said first information specified by said first detection time information of said first radiation detection signal contained in said first information; and
said second tomographic image information preparation device executes preparation of said second tomographic image information at each of said patient motion phases, by using said second information specified by said second detection time information of said second radiation detection signal contained in said second information.

15. The computed tomography device according to claim 11, comprising a radiation source position detecting device, which detects position of said radiation source in a rotation direction around said bed; wherein
said second tomographic image information preparation device uses a plurality of detected radiation source position information, to prepare said second tomographic image information.

16. The computed tomography device according to claim 11, comprising:
a rotation device, which rotates said radiation source around said bed;
a phase information preparation device, which receives input of measurement signals of patient motion of said patient, and prepares patient motion phase information to a plurality of said patient motion phases obtained by dividing said patient motion period, based on these measurement signals; and
a rotation control device, which controls rotation of said rotation device, based on said patient motion phase information.

17. The computed tomography device according to claim 11, wherein said radiation detector is a semiconductor radiation detector.

18. The computed tomography device according to claim 17, wherein any one of cadmium telluride (CdTe), cadmium zinc telluride (CZT), thallium bromide (TlBr), lead iodide ($PbI_2$) and gallium arsenide (GaAs) is used as an element material of said semiconductor radiation detector.

19. A computed tomography device comprising:
a bed for laying a patient;
a radiation source that rotates around said bed;
a plurality of radiation detectors, which are arranged around said bed, output a first radiation detection signal by detecting a first radiation emitted from said patient, caused by a radiopharmaceutical, and output a second detection radiation signal by detecting a second radiation emitted from said radiation source;
a radiation signal processing device that generates first information comprising first detection time information of said first radiation, first position information of said radiation detectors, from which said first radiation detection signal was output, and first energy information of said first radiation detection signal, from said first radiation detection signal, which was output from a plurality of said radiation detectors, and generates second information obtained from said second radiation, from said second radiation detection signal, which is output from a plurality of said radiation detectors;

a coincidence counting device that specifies a pair of said radiation detectors, which output said first radiation detection signal, within a setting period; by execution of coincidence counting, based on said detection time information contained in said plurality of first information;

a first tomographic image information preparation device that prepares a plurality of first tomographic image information at a plurality of patient motion phases obtained by dividing a patient motion period of said patient in terms of time, based on each of said first position information and said first detection time information of said specified pair of radiation detectors;

a radiation source position detection device that detects a position of said radiation source in a rotation direction around said bed;

a second tomographic image information preparation device that prepares second tomographic image information at a plurality of said patient motion phases, based on a plurality of said second information and a plurality of detected radiation source position information;

a relative displacement information generation device that determines relative displacement information among the second tomographic image information thereof, by superimposing, on said second tomographic image information at a certain one patient motion phase among a plurality of said patient motion phases, said second tomographic image information at other said patient motion phases; and a tomographic image information superimposing device that prepares superimposed first tomographic image information, by superimposing, on said first tomographic image information at a certain one said patient motion phase, said first tomographic image information at other said patient motion phases.

20. The computed tomography device according to claim 10, comprising:

said radiation signal processing device that generates said second information comprising said second detection time information of said second radiation, said second position information of said radiation detector, from which said second radiation detection signal was output, and said second energy information of said second radiation detection signal, from said second radiation detection signal, which was output from a plurality of said radiation detectors; and a discrimination device that receives input of said first information and said second information, and discriminates said first information and said second information by said first energy information and said second energy information; wherein said coincidence counting device executes said coincidence counting, by using said first detection time information of said discriminated first information; and said second tomographic image information preparation device executes preparation of said second tomographic image information, by using said discriminated second information.

* * * * *